(12) United States Patent
Klar et al.

(10) Patent No.: US 8,623,850 B2
(45) Date of Patent: Jan. 7, 2014

(54) 15, 16-METHYLENE-17-(1'-PROPENYL)-17,3'-OXIDOESTRA-4-EN-3-ONE DERIVATIVE, USE THEREOF, AND MEDICAMENT CONTAINING SAID DERIVATIVE

(75) Inventors: Ulrich Klar, Berlin (DE); Joachim Kuhnke, Potsdam (DE); Rolf Bohlmann, Berlin (DE); Jan Hübner, Berlin (DE); Sven Ring, Jena (DE); Thomas Frenzel, Hofheim (DE); Frederik Menges, Schriesheim (DE); Steffen Borden, Berlin (DE); Hans-Peter Muhn, Berlin (DE); Katja Prelle, Berlin (DE)

(73) Assignee: Bayer Intellectual Property GmbH, Monheim (DE)

( * ) Notice: Subject to any disclaimer, the term of this patent is extended or adjusted under 35 U.S.C. 154(b) by 440 days.

(21) Appl. No.: 12/810,857

(22) PCT Filed: Dec. 23, 2008

(86) PCT No.: PCT/EP2008/011164
§ 371 (c)(1),
(2), (4) Date: Aug. 31, 2010

(87) PCT Pub. No.: WO2009/083271
PCT Pub. Date: Jul. 9, 2009

(65) Prior Publication Data
US 2011/0003779 A1    Jan. 6, 2011

(30) Foreign Application Priority Data
Dec. 29, 2007  (DE) .......................... 10 2007 063 496

(51) Int. Cl.
A61K 31/56    (2006.01)
A61K 31/58    (2006.01)

(52) U.S. Cl.
USPC .......................................... 514/170; 514/182

(58) Field of Classification Search
USPC ................................................ 514/170, 182
See application file for complete search history.

(56) References Cited

U.S. PATENT DOCUMENTS

| | | |
|---|---|---|
| 4,870,069 A | 9/1989 | Ottow et al. |
| 4,912,097 A | 3/1990 | Teutsch et al. |
| 2008/0153787 A1 | 6/2008 | Bohlmann et al. |
| 2009/0029953 A1 | 1/2009 | Bohlmann et al. |

FOREIGN PATENT DOCUMENTS

| | | |
|---|---|---|
| DE | 10 2006 030 416 A1 | 1/2008 |
| EP | 0 245 170 A1 | 11/1987 |
| EP | 0 277 089 A1 | 8/1988 |
| WO | WO 2006/072467 A1 | 7/2006 |

OTHER PUBLICATIONS

International Search Report of PCT/EP2008/011164 (May 8, 2009).
K. Nickisch et al., "Aldosterone Antagonists. 4. Synthesis and Activities of Steroidal 6,6-Ethylene-15,16-Methylene 17-Spirolactones", Journal of Medicinal Chemistry, vol. 34 (1991) pp. 2464-2468.

*Primary Examiner* — San-Ming Hui
(74) *Attorney, Agent, or Firm* — Thomas C. Blankinship

(57) ABSTRACT

The invention relates to 15,16-methylene-17-(1'-propenyl)-17-3'-oxidoestra-4-en-3-one derivatives with the general chemical formula I, where the Z, $R^4$, $R^{6a}$, $R^{6b}$, $R^7$ and $R^{18}$ have the meanings stated in claim 1, and solvates, hydrates and salts thereof, including all crystal modifications and all stereoisomers of these compounds. The invention also relates to the use of these derivatives for the production of a drug for oral contraception and for the treatment of pre-, peri- and postmenopausal problems and drugs which contain such derivatives, in particular use in the aforesaid indications. The derivatives according to the invention have a progestational and in preferable cases also an antimineralcorticoid and neutral to slight androgenic activity.

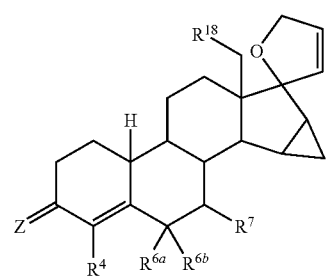

I

23 Claims, No Drawings

15,16-METHYLENE-17-(1'-PROPENYL)-17,3'-OXIDOESTRA-4-EN-3-ONE DERIVATIVE, USE THEREOF, AND MEDICAMENT CONTAINING SAID DERIVATIVE

The invention relates to novel 15,16-methylene-17-(1'-propenyl)-17-3'-oxidoestra-4-en-3-one derivatives with progestational action, the use thereof and drugs containing the derivatives, for example for the treatment of pre-, peri- and postmenopausal and also premenstrual problems.

From the literature, compounds with progestational, antimineralcorticoid, anti-androgenic or antiestrogenic action based on a steroid skeleton, which are for example derived from 19-nor-androst-4-en-3-one or a derivative thereof (the numbering of the steroid skeleton can for example be taken from Fresenius/Görlitzer 3$^{rd}$ Edn. 1991 "Organic Chemistry Nomenclature" p. 60 ff.) are known.

Thus WO 2006/072467 A1 discloses the compound with progestational action 6β,7β-15β,16β-dimethylene-3-oxo-17-pregn-4-en-21,17β-carbolactone (drospirenone), which has for example been used in an oral contraceptive and in a preparation for the treatment of postmenopausal problems. However, owing to its comparatively low affinity for the progestogen receptor and its comparatively high ovulation inhibitory dose, drospirenone is contained in the contraceptive at the relatively high daily dosage of 3 mg. Moreover, drospirenone is also characterized in that, in addition to the progestational action, it also has aldosterone-antagonistic (antimineralcorticoid) and antiandrogenic action. These two properties make drospirenone very similar in its pharmacological profile to the natural progestogen progesterone, which however, unlike drospirenone, is orally of insufficient bioavailability. In order to decrease the dosage to be administered, in WO 2006/072467 A1 an 18-methyl-19-nor-17-pregn-4-en-21,17-carbolactone and pharmaceutical preparations containing these, which have a higher progestational potency than drospirenone, are proposed.

Apart from this, for example U.S. Pat. No. 3,705,179 discloses steroids which have anti-androgenic activity and are suitable for the treatment of diseases which are connected with androgens.

Further, in EP 0 245 170 A1 steroid compounds are disclosed, in which an unsaturated spiro ether is contained in the 17 position and an aromatic residue in the 11 position.

The action of these compounds is stated to be progestomimetic or anti-progestomimetic, androgenic or anti-androgenic and anti-glucocorticoid.

The objective of the present invention is to provide compounds which exhibit strong binding to the progestogen receptor. In addition, the compounds should preferably also have an antimineralcorticoid action and neutral to slight androgenic action with regard to the androgen receptor. A further substantial target of the present invention also consists in achieving a balanced activity profile of the progestational action to the antimineralcorticoid action such that the ratio of the progestational to the antimineralcorticoid action is lower than with drospirenone.

This problem is solved by the 15,16-methylene-17-(t-propenyl)-17-3'-oxidoestra-4-en-3-one derivatives according to the invention according to claim 1, the use of the derivatives according to the invention according to claim 12 and a drug according to claim 14 containing at least one derivative according to the invention, in particular for oral contraception and for the treatment of pre-, peri- and postmenopausal problems. Advantageous embodiments of the invention are stated in the subclaims.

The numbering of the C skeleton of the derivatives according to the invention with the general chemical formula I follows the numbering of a steroid skeleton, for example described in Fresenius, loc, cit., in the usual manner. The numbering of the residues stated in the claims corresponds analogously to their binding position on the C skeleton of the derivatives, insofar as this relates to $R^4$, $R^6$, $R^7$ and $R^{18}$. Thus for example the residue $R^4$ is bound to the $C^4$ position of the derivative according to the invention.

With regard to the groups defined as Z, the groups NOR' and NNHSO$_2$R' each bind with a double bond via N to the C skeleton of the derivative as to =NOR' or =NNH—SO$_2$R' respectively. OR' in NOR' and NHSO$_2$R' in NNHSO$_2$R' can be in the syn or anti position.

Alkyl in R', $R^{6a}$, $R^{6b}$, $R^7$, $R^{18}$, $R^{19}$, $R^{20}$, $R^{21a}$, $R^{21b}$ and $R^{22}$ and in other cases should be understood to mean linear or branched-chain alkyl groups with the stated number of carbon atoms or optionally 1-10 carbon atoms, such as for example methyl, ethyl, propyl, isopropyl, butyl, isobutyl, tert.-butyl, pentyl, isopentyl, neopentyl, hexyl, heptyl or decyl. Alkyl in $R^{18}$ should in particular be understood to mean methyl, ethyl, propyl or isopropyl and $R^{22}$ methyl, ethyl, propyl, isopropyl, butyl, isobutyl, tert.-butyl, pentyl, isopentyl, neopentyl or hexyl. Further, the alkyl groups R', $R^{6a}$, $R^{6b}$, $R^7$, $R^{18}$, $R^{19}$, $R^{20}$, $R^{21a}$, $R^{21b}$ and $R^{22}$ can be perfluorinated or substituted with 1-5 halogen atoms, hydroxy groups, $C_1$-$C_4$ alkoxy groups or $C_6$-$C_{12}$ aryl groups (which in turn can be substituted with 1-3 halogen atoms). In particular, alkyl can therefore also stand for hydroxymethylene (HO—CH$_2$), hydroxyethylene (HO—C$_2$H$_4$), hydroxypropylene (HO—C$_3$H$_6$) and hydroxy-butylene (HO—C$_4$H$_8$) and isomers thereof.

Alkenyl in $R^{6a}$, $R^{6b}$ and $R^7$ should be understood to mean linear or branched-chain alkenyl groups with 2-10 carbon atoms, such as for example vinyl, propenyl, butenyl, pentenyl, isobutenyl or isopentenyl.

Alkynyl in $R^{6a}$, $R^{6b}$ and $R^7$ should be understood to mean linear or branched-chain alkynyl groups with 2-10 carbon atoms, such as for example ethynyl, propynyl, butynyl, pentynyl, isobutynyl or isopentynyl.

The alkenyl and alkynyl groups $R^{6a}$, $R^{6a}$ and $R^7$ can be substituted with 1-5 halogen atoms, hydroxy groups, $C_1$-$C_3$ alkoxy groups or $C_6$-$C_{12}$ aryl groups (which in turn can be substituted with 1-3 halogen atoms).

Cycloalkyl in $R^7$ should be understood to mean cycloalkyl groups with 3-6 carbon atoms, for example cyclopropyl, cyclobutyl, cyclopentyl and cyclohexyl. The cycloalkyl groups $R^7$ can be substituted with halogen, OH, O-alkyl, CO$_2$H, CO$_2$-alkyl, NH$_2$, NO$_2$, N$_3$, CN, $C_1$-$C_{10}$ alkyl, $C_1$-$C_{10}$ acyl or $C_1$-$C_{10}$ acyloxy groups.

Aryl in R' and in other cases should be understood to mean substituted and unsubstituted carbocyclic or heterocyclic residues with one or more hetero atoms, such as for example phenyl, naphthyl, furyl, thienyl, pyridyl, pyrazolyl, pyrimidinyl, oxazolyl, pyridazinyl, pyrazinyl, quinolyl or thiazolyl, which can be singly or multiply substituted with halogen, OH, O-alkyl, CO$_2$H, CO$_2$-alkyl, NH$_2$, NO$_2$, N$_3$, CN, $C_1$-$C_{10}$ alkyl, $C_1$-$C_{10}$ acyl or $C_1$-$C_{10}$ acyloxy groups. Insofar as aryl is otherwise mentioned as a substituent on alkyl, alkenyl or alkynyl, these are in particular aryl groups with 6-12 ring carbon atoms.

Aralkyl in R' should be understood to mean aralkyl groups which can contain up to 14 carbon atoms, preferably 6 to 10 C atoms, in the ring, and 1 to 8, preferably 1 to 4, carbon atoms, in the alkyl chain. Possible aralkyl residues are for example benzyl, phenylethyl, naphthylmethyl, naphthylethyl, furylmethyl, thienylethyl or pyridylpropyl. The rings can be singly or multiply substituted with halogen, OH, O-alkyl, $CO_2H$, $CO_2$-alkyl, $NO_2$, $N_3$, CN, $C_1$-$C_{20}$ alkyl, $C_1$-$C_{20}$ acyl or $C_1$-$C_{20}$ acyloxy groups.

Insofar as alkoxy (O-alkyl) is mentioned, these are alkoxy groups with 1-4 carbon atoms. Alkoxy can in particular be methoxy, ethoxy and propoxy.

Insofar as acyl (CO-alkyl) is mentioned, these are acyl groups with 1-20 carbon atoms. Acyl can in particular be formyl, acetyl, propionyl and butyryl.

Insofar as acyloxy (O—CO-alkyl) is mentioned, these are acyloxy groups with 1-20 carbon atoms. Acyloxy can in particular be formyloxy, acetyloxy, propionyloxy and butyryloxy.

Halogen means fluorine, chlorine or bromine. Among these, chlorine is preferable.

The present invention relates to 15,16-methylene-17-(1'-propenyl)-17-3'-oxidoestra-4-en-3-one derivatives with the general chemical formula I:

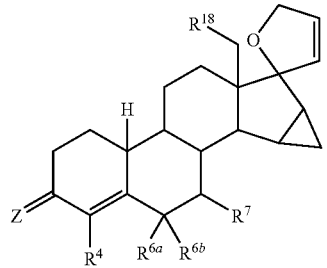

in which

Z is selected from the group comprising oxygen, two hydrogen atoms, NOR' and $NNHSO_2R'$, where R' is hydrogen, $C_1$-$C_{10}$ alkyl, aryl or $C_7$-$C_{20}$ aralkyl, $R^4$ is selected from the group comprising hydrogen and halogen, and further, either:

$R^{6a}$, $R^{6b}$ are each mutually independently selected from the group comprising hydrogen, $C_1$-$C_{10}$ alkyl, $C_2$-$C_{10}$ alkenyl and $C_2$-$C_{10}$ alkynyl, or together form methylene or 1,2-ethanediyl and $R^7$ is selected from the group comprising hydrogen, $C_1$-$C_{10}$ alkyl, $C_3$-$C_6$ cycloalkyl, $C_2$-$C_{10}$ alkenyl and $C_2$-$C_{10}$ alkynyl, or:

$R^{6a}$, $R^7$ together comprise oxygen or a methylene group or are omitted with the formation of a double bond between $C^6$ and $C^7$ and $R^{6b}$ is selected from the group comprising hydrogen, $C_1$-$C_{10}$ alkyl, $C_2$-$C_{10}$ alkenyl and $C_2$-$C_{10}$ alkynyl, and $R^{18}$ is selected from the group comprising hydrogen and $C_1$-$C_3$ alkyl.

Further, the invention also relates to the solvates, hydrates and salts of the derivatives according to the invention, including all crystal modifications and all stereoisomers of these derivatives.

According to a preferred embodiment of the invention, Z is selected from the group comprising oxygen, NOR' and $NNHSO_2R'$.

According to a further preferred embodiment of the invention, Z stands for oxygen.

According to a further preferred embodiment of the invention, $R^4$ is selected from the group comprising hydrogen and chlorine.

According to a further preferred embodiment of the invention, $R^{6a}$ and $R^{6b}$ together form 1,2-ethanediyl or are each hydrogen.

According to a further preferred embodiment of the invention, $R^7$ is selected from the group comprising hydrogen, methyl, ethyl and vinyl.

According to a further preferred embodiment of the invention, $R^{6a}$ and $R^7$ together comprise a methylene group.

According to a further preferred embodiment of the invention, $R^{6a}$ and $R^7$ are omitted with the formation of a double bond between $C^6$ and $C^7$.

According to a further preferred embodiment of the invention, $R^{18}$ is selected from the group comprising hydrogen and methyl.

Particularly preferred are compounds with the general chemical formula I, in which:

is oxygen or NOR', where R' is hydrogen, $C_1$-$C_6$ alkyl, aryl or $C_7$-$C_{12}$ aralkyl, $R^4$ is hydrogen or halogen, and further, either:

$R^{6a}$, $R^{6b}$ are each mutually independently selected from the group comprising hydrogen, $C_1$-$C_6$ alkyl, $C_2$-$C_6$ alkenyl and $C_2$-$C_6$ alkynyl, or together form methylene or 1,2-ethanediyl and $R^7$ is hydrogen, $C_1$-$C_6$ alkyl, $C_3$-$C_6$ cycloalkyl, $C_2$-$C_6$ alkenyl or $C_2$-$C_6$ alkynyl, or:

$R^{6a}$, $R^7$ together comprise a methylene group or are omitted with the formation of a double bond between $C^6$ and $C^7$ and $R^{6b}$ is hydrogen, $C_1$-$C_6$ alkyl, $C_2$-$C_6$ alkenyl or $C_2$-$C_6$ alkynyl and $R^{18}$ is hydrogen or $C_1$-$C_2$ alkyl, where in this case also the solvates, hydrates and salts of the derivatives according to the invention, including all crystal modifications and all stereoisomers of these derivatives, are included.

Also particularly preferred are compounds with the general chemical formula I, in which Z is oxygen or NOR', where R' is hydrogen or $C_1$-$C_3$ alkyl, $R^4$ is hydrogen, chlorine or bromine, and further, either:

$R^{6a}$, $R^{6b}$ are each mutually independently selected from the group comprising hydrogen, $C_1$-$C_3$ alkyl and $C_2$-$C_4$ alkenyl, or together form methylene or 1,2-ethanediyl and $R^7$ is hydrogen, $C_1$-$C_4$ alkyl, $C_3$-$C_4$ cycloalkyl or $C_2$-$C_4$ alkenyl, or:

$R^{6a}$, $R^7$ together comprise a methylene group or are omitted with the formation of a double bond between $C^6$ and $C^7$ and $R^{6b}$ is hydrogen, $C_1$-$C_3$ alkyl or $C_2$-$C_4$ alkenyl and $R^{18}$ is hydrogen or methyl, where in this case also the solvates, hydrates and salts of the derivatives according to the invention, including all crystal modifications and all stereoisomers of these derivatives, are included.

Herewith, all possible stereoisomers and isomer mixtures, including racemates, of the compounds with the general chemical formula I are also expressly included. Each of the stated substituents on the basic steroid skeleton can be present both in an β and also in a β position. In addition, the substituents on the basic steroid skeleton which contain a double bond and in which the double bond bears at least one substituent which is not hydrogen at each carbon atom can be present in the E and also in the Z configuration. Groups bound to two adjacent carbon atoms of the skeleton, for example an oxygen atom, methylene or 1,2-ethanediyl, are bound either in the α,α position or in the β,β position.

Also expressly included are all crystal modifications of the compound with the general chemical formula I.

Also expressly included are derivatives according to the invention in the form of solvates, in particular of hydrates, where the compounds according to the invention accordingly contain polar solvents, in particular water, as a structural element of the crystal lattice of the compounds according to the invention. The polar solvent, in particular water, can be present in a stoichiometric or also nonstoichiometric ratio. Stoichiometric solvates and hydrates are also referred to as hemi-, (semi-), mono-, sesqui-, di-, tri-, tetra-, penta-, etc. solvates or hydrates.

If an acidic group is present, the physiologically compatible salts of organic and inorganic bases are suitable as salts, such as for example the readily soluble alkali metal and alkaline earth salts, and the salts of N-methyl-glucamine, D-methyl-glucamine, ethyl-glucamine, lysine, 1,6-hexadiamine, ethanolamine, glucosamine, sarcosine, serinol, trishydroxy-methyl-aminomethane, aminopropanediol, Sovak base and 1-amino-2,3,4-butanetriol. If a basic function is present, the physiologically compatible salts of organic and inorganic acids, such as those of hydrochloric acid, sulfuric acid, phosphoric acid, citric acid, tartaric acid and the like are suitable.

It has been found that the compounds and derivatives according to the invention have good progestational activity. In addition, some interesting compounds according to the invention interact with the mineralcorticoid receptor and are capable of mediating an antagonistic action. Further, the compounds according to the invention exhibit neutral to slight androgenic activity with regard to the androgen receptor. A further property of the vast majority of the compounds consists in that the binding of these compounds to the progesterone receptor and to the mineralcorticoid receptor is mutually relatively balanced, i.e. such that with them the ratio of the binding capacity to the progesterone receptor to the binding capacity to the mineralcorticoid receptor is lower than with drospirenone. Thus the antimineralcorticoid action of these compounds with a given progestational action is less than with drospirenone. If the dosage of a given compound according to the invention is established on the basis of its progestational action, then the antimineralcorticoid action of this compound at this dosage is lower than with drospirenone.

The compounds named below are particularly preferable (reference is also made to the synthetic examples described later below):

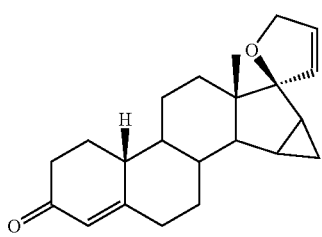

17α-(1'-propenyl)-15α, 16α-methylene-17β-3'-oxidoestra-4-en-3-one (Example 12)
17α-(1'-propenyl)-15β, 16β-methylene-17β-3'-oxidoestra-4-en-3-one (Example 8)

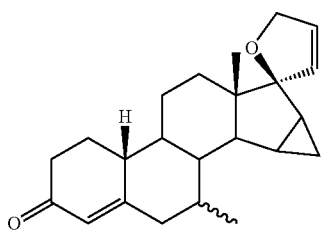 [SMILES: CC1CC2=CC(=O)CC[C@@H]2C2CC[C@@]3(C)C(C4CC4[C@@]34C=CCO4)C12]

7α-methyl-15α, 16α-methylene-17α-(1'-propenyl)-17β-3'-oxidoestra-4-en-3-one (Example 14)
7α-methyl-15β, 16β-methylene-17α-(1'-propenyl)-17β-3'-oxidoestra-4-en-3-one 7β-methyl-15α, 16α-methylene-17α-(1'-propenyl)-17β-3'-oxidoestra-4-en-3-one
7β-methyl-15β, 16β-methylene-17α-(1'-propenyl)-17β-3'-oxidoestra-4-en-3-one

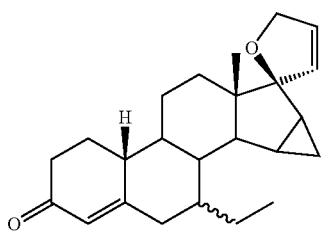

7α-ethyl-15α, 16α-methylene-17α-(1'-propenyl)-17β-3'-oxidoestra-4-en-3-one (Example 15A)
7α-ethyl-15β, 16β-methylene-17α-(1'-propenyl)-17β-3'-oxidoestra-4-en-3-one 7β-ethyl-15α, 16α-methylene-17α-(1'-propenyl)-17β-3'-oxidoestra-4-en-3-one (Example 15B)
7β-ethyl-15β, 16β-methylene-17α-(1'-propenyl)-17β-3'-oxidoestra-4-en-3-one

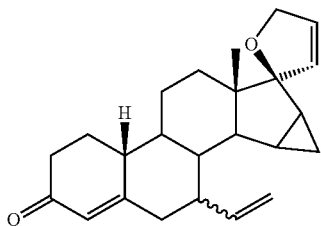

7α-vinyl-15α, 16α-methylene-17α-(1'-propenyl)-17β-3'-oxidoestra-4-en-3-one (Example 16A)
7α-vinyl-15β, 16β-methylene-17α-(1'-propenyl)-17β-3'-oxidoestra-4-en-3-one 7β-vinyl-15α, 16α-methylene-17α-(1'-propenyl)-17β-3'-oxidoestra-4-en-3-one (Example 16B)
7β-vinyl-15β, 16β-methylene-17α-(1'-propenyl)-17β-3'-oxidoestra-4-en-3-one

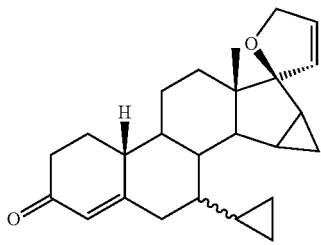

7α-cyclopropyl-15α, 16α-methylene-17α-(1'-propenyl)-17β-3'-oxidoestra-4-en-3-one (Example 17A)
7α-cyclopropyl-15β, 16β-methylene-17α-(1'-propenyl)-17β-3'-oxidoestra-4-en-3-one 7β-cyclopropyl-15α, 16α-methylene-17α-(1'-propenyl)-17β-3'-oxidoestra-4-en-3-one (Example 17B)
7β-cyclopropyl-15β, 16β-methylene-17α-(1'-propenyl)-17β-3'-oxidoestra-4-en-3-one

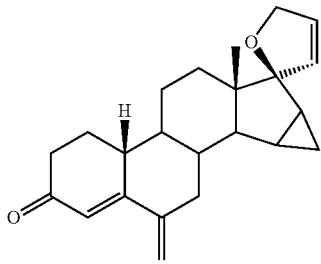

6-methylene-15α, 16α-methylene-17α-(1'-propenyl)-17β-3'-oxidoestra-4-en-3-one
6-methylene-15β, 16β-methylene-17α-(1'-propenyl)-17β-3'-oxidoestra-4-en-3-one

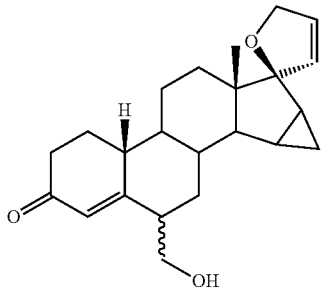

6α-hydroxymethylene-15α, 16α-methylene-17α-(1'-propenyl)-17β-3'-oxidoestra-4-en-3-one
6α-hydroxymethylene-15β, 16β-methylene-17α-(1'-propenyl)-17β-3'-oxidoestra-4-en-3-one 6β-hydroxymethylene-15α, 16α-methylene-17α-(1'-propenyl)-17β-3'-oxidoestra-4-en-3-one
6β-hydroxymethylene-15β, 16β-methylene-17α-(1'-propenyl)-17β-3'-oxidoestra-4-en-3-one

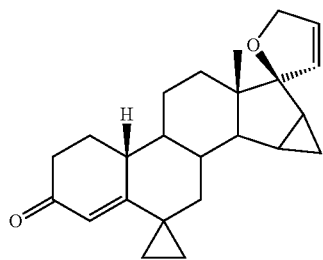
6,6-(1,2-ethanediyl)-15α, 16α-methylene-17α-(1'-propenyl)-17β-3'-oxidoestra-4-en-3-one
6,6-(1,2-ethanediyl)-15β, 16β-methylene-17α-(1'-propenyl)-17β-3'-oxidoestra-4-en-3-one

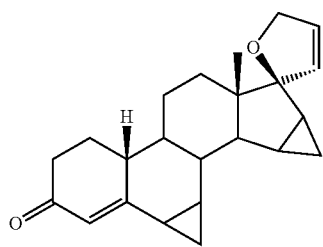
6α, 7α; 15α, 16α-bismethylene-17α-(1'-propenyl)-17β-3'-oxidoestra-4-en-3-one
6β, 7β; 15α, 16α-bismethylene-17α-(1'-propenyl)-17β-3'-oxidoestra-4-en-3-one
6α, 7α; 15β, 16β-bismethylene-17α-(1'-propenyl)-17β-3'-oxidoestra-4-en-3-one
6β, 7β; 15β, 16β-bismethylene-17α-(1'-propenyl)-17β-3'-oxidoestra-4-en-3-one

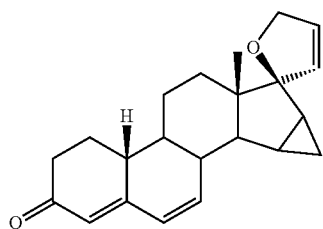
17α-(1'-propenyl)-15α, 16α-methylene-17β-3'-oxidoestra-4,6-dien-3-one (Example 13)
17α-(1'-propenyl)-15β, 16β-methylene-17β-3'-oxidoestra-4,6-dien-3-one (Example 11)

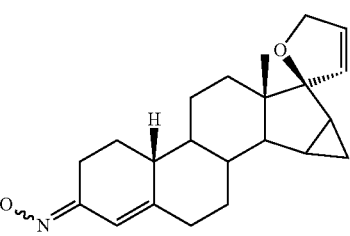
(E/Z)-3-(hydroxyimino)-17α-(1'-propenyl)-15α, 16α-methylene-17β-3'-oxidoestra-4-ene
(E/Z)-3-(hydroxyimino)-17α-(1'-propenyl)-15β, 16β-methylene-17β-3'-oxidoestra-4-ene

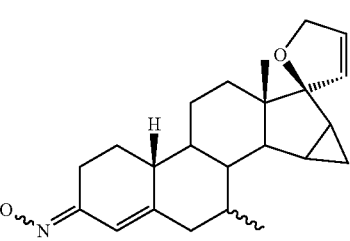
(E/Z)-3-(hydroxyimino)-7α-methyl-15α, 16α-methylene-17α-(1'-propenyl)-17β-3'-oxidoestra-4-ene
(E/Z)-3-(hydroxyimino)-7α-methyl-15β, 16β-methylene-17α-(1'-propenyl)-17β-3'-oxidoestra-4-ene

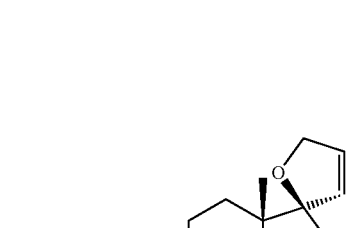
(E/Z)-3-(hydroxyimino)-7β-methyl-15α, 16α-methylene-17α-(1'-propenyl)-17β-3'-oxidoestra-4-ene
(E/Z)-3-(hydroxyimino)-7β-methyl-15β, 16β-methylene-17α-(1'-propenyl)-17β-3'-oxidoestra-4-ene

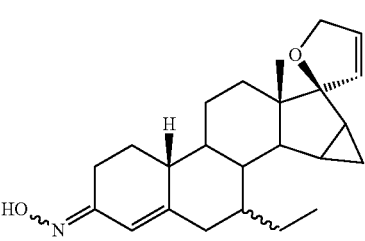
(E/Z)-3-(hydroxyimino)-7α-ethyl-15α, 16α-methylene-17α-(1'-propenyl)-17β-3'-oxidoestra-4-ene
(E/Z)-3-(hydroxyimino)-7α-ethyl-15β, 16β-methylene-17α-(1'-propenyl)-17β-3'-oxidoestra-4-ene (E/Z)-3-(hydroxyimino)-7β-ethyl-15α, 16α-methylene-17α-(1'-propenyl)-17β-3'-oxidoestra-4-ene (E/Z)-3-(hydroxyimino)-7β-ethyl-15β, 16β-methylene-17α-(1'-propenyl)-17β-3'-oxidoestra-4-ene (E/Z)-3-(hydroxyimino)-7α-vinyl-15α, 16α-methylene-17α,-(1'-propenyl)-17β-3'-oxidoestra-4-ene (E/Z)-3-(hydroxyimino)-7α-vinyl-15β, 16β-methylene-17α-(1'-propenyl)-17β-3'-oxidoestra-4-ene (E/Z)-3-(hydroxyimino)-7β-vinyl-15α, 16α-methylene-17α-(1'-propenyl)-17β-3'-oxidoestra-4-ene (E/Z)-3-(hydroxyimino)-7β-vinyl-15β, 16β-methylene-17α-(1'-propenyl)-17β-3'-oxidoestra-4-ene

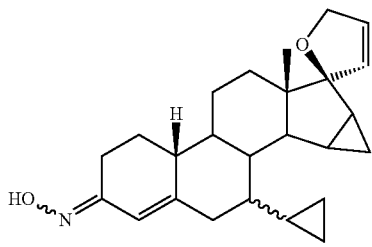

(E/Z)-3-(hydroxyimino)-7α-cyclopropyl-15α, 16α-methylene-17α-(1'-propenyl)-17β-3'-oxidoestra-4-ene
(E/Z)-3-(hydroxyimino)-7α-cyclopropyl-15β, 16β-methylene-17α-(1'-propenyl)-17β-3'-oxidoestra-4-ene (E/Z)-3-(hydroxyimino)-7β-cyclopropyl-15α, 16α-methylene-17α-(1'-propenyl)-17β-3'-oxidoestra-4-ene
(E/Z)-3-(hydroxyimino)-7β-cyclopropyl-15β, 16β-methylene-17α-(1'-propenyl)-17β-3'-oxidoestra-4-ene

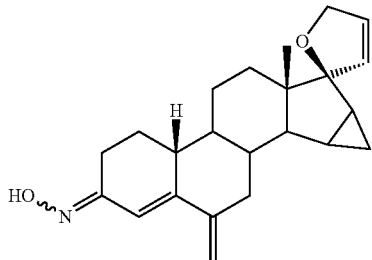

(E/Z)-3-(hydroxyimino)-6-methylene-17α-(1'-propenyl)-15α, 16α-methylene-17β-3'-oxidoestra-4-ene
(E/Z)-3-(hydroxyimino)-6-methylene-17α-(1'-propenyl)-15β, 16β-methylene-17β-3'-oxidoestra-4-ene

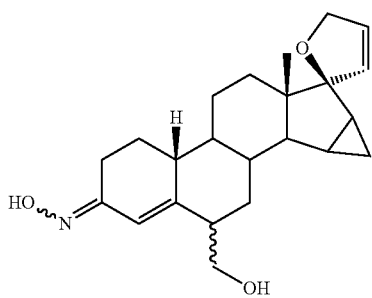

(E/Z)-3-(hydroxyimino)-6α-hydroxymethylene-17α-(1'-propenyl)-15α,16α-methylene-17β-3'-oxidoestra-4-ene
(E/Z)-3-(hydroxyimino)-6α-hydroxymethylene-17α-(1'-propenyl)-15β, 16β-methylene-17β-3'-oxidoestra-4-ene (E/Z)-3-(hydroxyimino)-6β-hydroxymethylene-17α-(1'-propenyl)-15α, 16α-methylene-17β-3'-oxidoestra-4-ene
(E/Z)-3-(hydroxyimino)-6β-hydroxymethylene-17α-(1'-propenyl)-15β, 16β-methylene-17β-3'-oxidoestra-4-ene

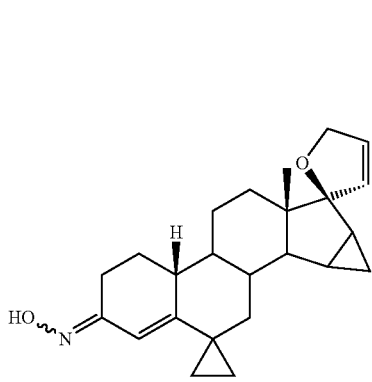

(E/Z)-3-(hydroxyimino)-6,6-(1,2-ethandiyl)-17α-(1'-propenyl)-15α, 16α-methylene-17β-3'-oxidoestra-4-ene
(E/Z)-3-(hydroxyimino)-6,6-(1,2-ethandiyl)-17α-(1'-propenyl)-15β, 16β-methylene-17β-3'-oxidoestra-4-ene

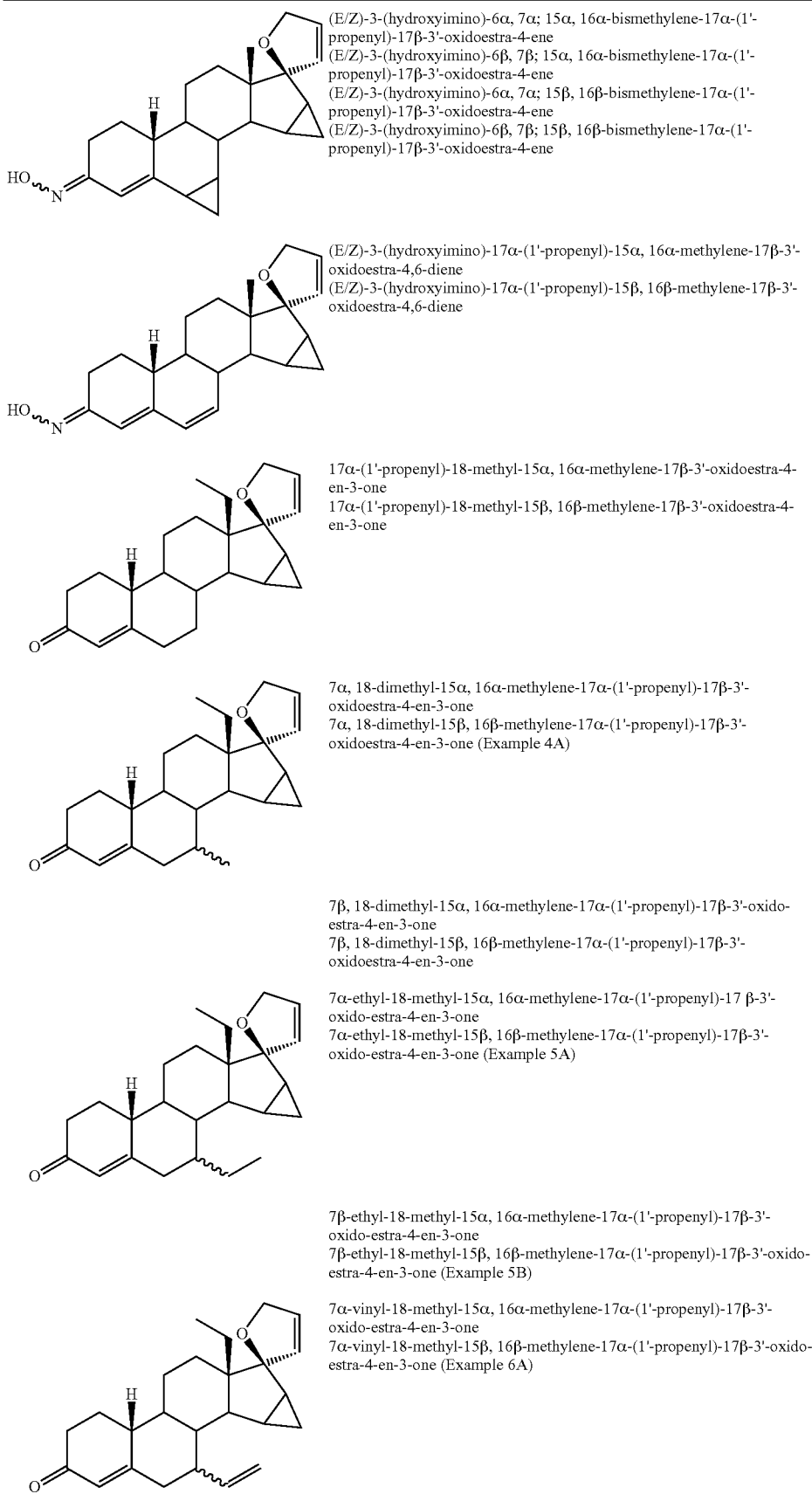

(E/Z)-3-(hydroxyimino)-6α, 7α; 15α, 16α-bismethylene-17α-(1'-propenyl)-17β-3'-oxidoestra-4-ene
(E/Z)-3-(hydroxyimino)-6β, 7β; 15α, 16α-bismethylene-17α-(1'-propenyl)-17β-3'-oxidoestra-4-ene
(E/Z)-3-(hydroxyimino)-6α, 7α; 15β, 16β-bismethylene-17α-(1'-propenyl)-17β-3'-oxidoestra-4-ene
(E/Z)-3-(hydroxyimino)-6β, 7β; 15β, 16β-bismethylene-17α-(1'-propenyl)-17β-3'-oxidoestra-4-ene (E/Z)-3-(hydroxyimino)-17α-(1'-propenyl)-15α, 16α-methylene-17β-3'-oxidoestra-4,6-diene
(E/Z)-3-(hydroxyimino)-17α-(1'-propenyl)-15β, 16β-methylene-17β-3'-oxidoestra-4,6-diene 17α-(1'-propenyl)-18-methyl-15α, 16α-methylene-17β-3'-oxidoestra-4-en-3-one
17α-(1'-propenyl)-18-methyl-15β, 16β-methylene-17β-3'-oxidoestra-4-en-3-one 7α, 18-dimethyl-15α, 16α-methylene-17α-(1'-propenyl)-17β-3'-oxidoestra-4-en-3-one
7α, 18-dimethyl-15β, 16β-methylene-17α-(1'-propenyl)-17β-3'-oxidoestra-4-en-3-one (Example 4A)

7β, 18-dimethyl-15α, 16α-methylene-17α-(1'-propenyl)-17β-3'-oxido-estra-4-en-3-one
7β, 18-dimethyl-15β, 16β-methylene-17α-(1'-propenyl)-17β-3'-oxidoestra-4-en-3-one 7α-ethyl-18-methyl-15α, 16α-methylene-17α-(1'-propenyl)-17β-3'-oxido-estra-4-en-3-one
7α-ethyl-18-methyl-15β, 16β-methylene-17α-(1'-propenyl)-17β-3'-oxido-estra-4-en-3-one (Example 5A)

7β-ethyl-18-methyl-15α, 16α-methylene-17α-(1'-propenyl)-17β-3'-oxido-estra-4-en-3-one
7β-ethyl-18-methyl-15β, 16β-methylene-17α-(1'-propenyl)-17β-3'-oxido-estra-4-en-3-one (Example 5B)

7α-vinyl-18-methyl-15α, 16α-methylene-17α-(1'-propenyl)-17β-3'-oxido-estra-4-en-3-one
7α-vinyl-18-methyl-15β, 16β-methylene-17α-(1'-propenyl)-17β-3'-oxido-estra-4-en-3-one (Example 6A)

7β-vinyl-18-methyl-15α, 16α-methylene-17α-(1'-propenyl)-17β-3'-oxido-estra-4-en-3-one
7β-vinyl-18-methyl-15β, 16β-methylene-17α-(1'-propenyl)-17β-3'-oxido-estra-4-en-3-one

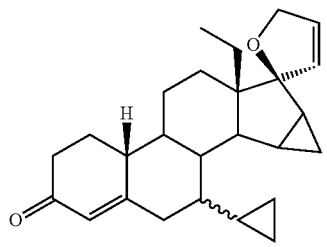

7α-cyclopropyl-18-methyl-15α, 16α-methylene-17α-(1'-propenyl)-17β-3'-oxidoestra-4-en-3-one
7α-cyclopropyl-18-methyl-15β, 16β-methylene-17α-(1'-propenyl)-17β,-3'-oxidoestra-4-en-3-one (Example 7A)

7β-cyclopropyl-18-methyl-15α, 16α-methylene-17α-(1'-propenyl)-17β-3'-oxidoestra-4-en-3-one
7β-cyclopropyl-18-methyl-15β, 16β-methylene-17α-(1'-propenyl)-17β-3'-oxidoestra-4-en-3-one

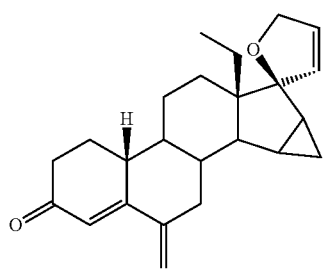

6-methylene-18-methyl-15α, 16α-methylene-17α-(1'-propenyl)-17β-3'-oxidoestra-4-en-3-one
6-methylene-18-methyl-15β, 16β-methylene-17α-(1'-propenyl)-17β-3'-oxidoestra-4-en-3-one

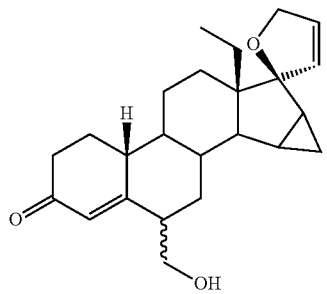

6α-hydroxymethylene-18-methyl-15α, 16α-methylene-17α-(1'-propenyl)-17β-3'-oxidoestra-4-en-3-one
6α-hydroxymethylene-18-methyl-15β, 16β-methylene-17α-(1'-propenyl)-17β-3'-oxidoestra-4-en-3-one

6β-hydroxymethylene-18-methyl-15α, 16α-methylene-17α-(1'-propenyl)-17β-3'-oxidoestra-4-en-3-one
6β-hydroxymethylene-18-methyl-15β, 16β-methylene-17α-(1'-propenyl)-17β-3'-oxidoestra-4-en-3-one (Example 9)

6,6-(1,2-ethanediyl)-18-methyl-15α, 16α-methylene-17α-(1'-propenyl)-17β-3'-oxidoestra-4-en-3-one
6,6-(1,2-ethanediyl)-18-methyl-15β, 16β-methylene-17α-(1'-propenyl)-17β-3'-oxidoestra-4-en-3-one (Example 10)

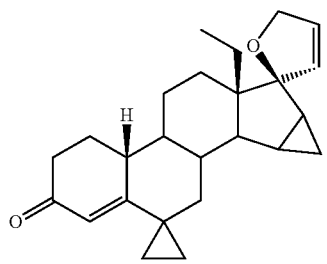

-continued

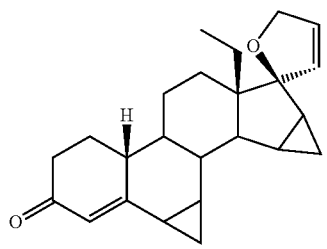
6α, 7α; 15α, 16α-bismethylene-18-methyl-17α-(1'-propenyl)-17β-3'-oxido-estra-4-en-3-one
6β, 7β; 15α, 16α-bismethylene-18-methyl-17α-(1'-propenyl)-17β-3'-oxido-estra-4-en-3-one
6α, 7α; 15β, 16β-bismethylene-18-methyl-17α-(1'-propenyl)-17β-3'-oxido-estra-4-en-3-one (Example 2)
6β, 7β; 15β, 16β-bismethylene-18-methyl-17α-(1'-propenyl)-17β-3'-oxido-estra-4-en-3-one (Example 1)

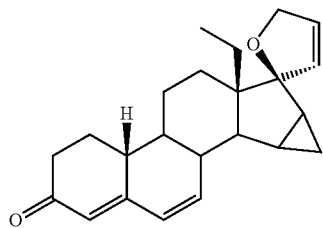
17α-(1'-propenyl)-18-methyl-15α, 16α-methylene-17β-3'-oxidoestra-4,6-dien-3-one
17α-(1'-propenyl)-18-methyl-15β, 16β-methylene-17β-3'-oxidoestra-4,6-dien-3-one (Example 3)

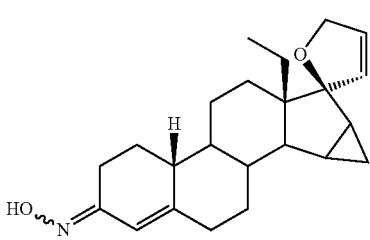
(E/Z)-3-(hydroxyimino)-18-methyl-17α-(1'-propenyl)-15α, 16α-methylene-17β-3'-oxidoestra-4-ene
(E/Z)-3-(hydroxyimino)-18-methyl-17α-(1'-propenyl)-15β, 16β-methylene-17β-3'-oxidoestra-4-ene

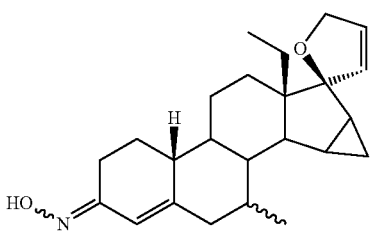
(E/Z)-3-(hydroxyimino)-7α, 18-bismethyl-15α, 16α-methylene-17α-(1'-propenyl)-17β-3'-oxidoestra-4-ene
(E/Z)-3-(hydroxyimino)-7α, 18-bismethyl-15β, 16β-methylene-17α-(1'-propenyl)-17β-3'-oxidoestra-4-ene (E/Z)-3-(hydroxyimino)-7β, 18-bismethyl-15α, 16α-methylene-17α-(1'-propenyl)-17β-3'-oxidoestra-4-ene
(E/Z)-3-(hydroxyimino)-7β, 18-bismethyl-15β, 16β-methylene-17α-(1'-propenyl)-17β-3'-oxidoestra-4-ene

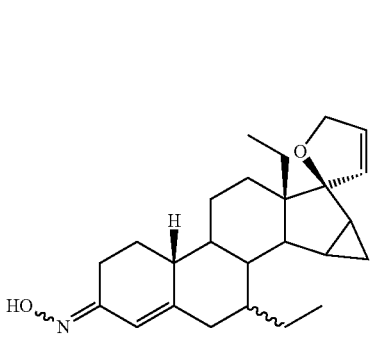
(E/Z)-3-(hydroxyimino)-7α-ethyl-18-methyl-15α, 16α-methylene-17α-(1'-propenyl)-17β-3'-oxidoestra-4-ene
(E/Z)-3-(hydroxyimino)-7α-ethyl-18-methyl-15β, 16β-methylene-17α-(1'-propenyl)-17β-3'-oxidoestra-4-ene (E/Z)-3-(hydroxyimino)-7β-ethyl-18-methyl-15α, 16α-methylene-17α-(1'-propenyl)-17β-3'-oxidoestra-4-ene
(E/Z)-3-(hydroxyimino)-7β-ethyl-18-methyl-15β, 16β-methylene-17α-(1'-propenyl)-17β-3'-oxidoestra-4-ene (E/Z)-3-(hydroxyimino)-7α-vinyl-18-methyl-15α, 16α-methylene-17α-(1'-propenyl)-17β-3'-oxidoestra-4-ene
(E/Z)-3-(hydroxyimino)-7α-vinyl-18-methyl-15β, 16β-methylene-17α-(1'-propenyl)-17β-3'-oxidoestra-4-ene (E/Z)-3-(hydroxyimino)-7β-vinyl-18-methyl-15α, 16α-methylene-17α-(1'-propenyl)-17β-3'-oxidoestra-4-ene
(E/Z)-3-(hydroxyimino)-7β-vinyl-18-methyl-15β, 16β-methylene-17α-(1'-propenyl)-17β-3'-oxidoestra-4-ene

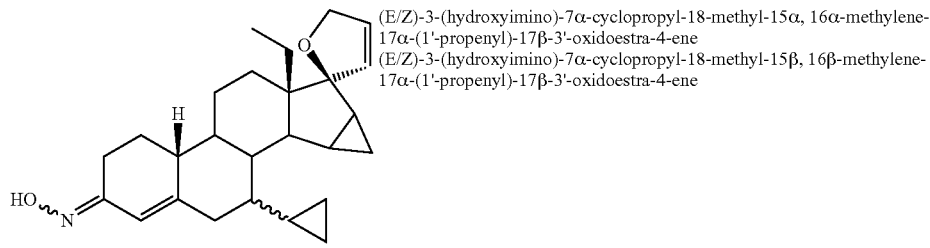

(E/Z)-3-(hydroxyimino)-7α-cyclopropyl-18-methyl-15α, 16α-methylene-17α-(1'-propenyl)-17β-3'-oxidoestra-4-ene
(E/Z)-3-(hydroxyimino)-7α-cyclopropyl-18-methyl-15β, 16β-methylene-17α-(1'-propenyl)-17β-3'-oxidoestra-4-ene (E/Z)-3-(hydroxyimino)-7β-cyclopropyl-18-methyl-15α, 16α-methylene-17α-(1'-propenyl)-17β-3'-oxidoestra-4-ene
(E/Z)-3-(hydroxyimino)-7β-cyclopropyl-18-methyl-15β, 16β-methylene-17α-(1'-propenyl)-17β-3'-oxidoestra-4-ene

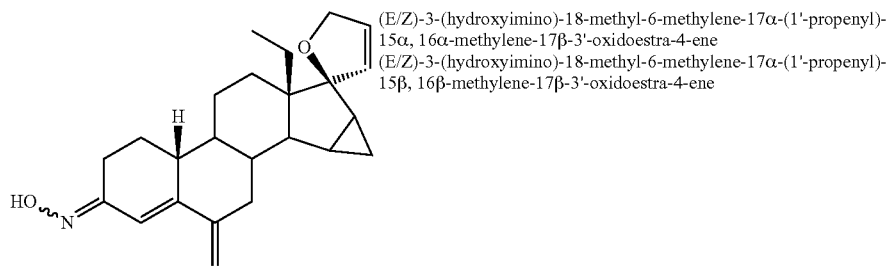

(E/Z)-3-(hydroxyimino)-18-methyl-6-methylene-17α-(1'-propenyl)-15α, 16α-methylene-17β-3'-oxidoestra-4-ene
(E/Z)-3-(hydroxyimino)-18-methyl-6-methylene-17α-(1'-propenyl)-15β, 16β-methylene-17β-3'-oxidoestra-4-ene

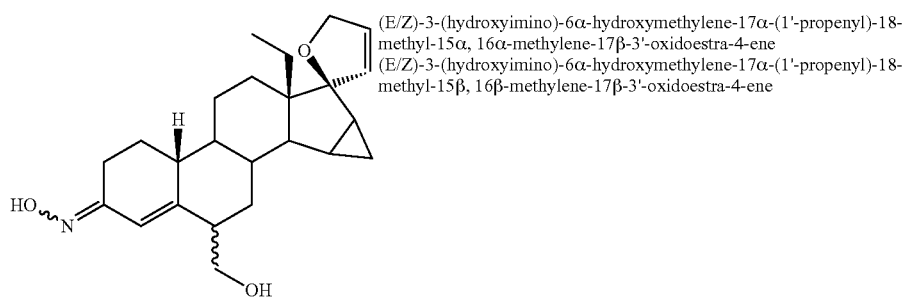

(E/Z)-3-(hydroxyimino)-6α-hydroxymethylene-17α-(1'-propenyl)-18-methyl-15α, 16α-methylene-17β-3'-oxidoestra-4-ene
(E/Z)-3-(hydroxyimino)-6α-hydroxymethylene-17α-(1'-propenyl)-18-methyl-15β, 16β-methylene-17β-3'-oxidoestra-4-ene (E/Z)-3-(hydroxyimino)-6β-hydroxymethylene-17α,-(1'-propenyl)-18-methyl-15α, 16α-methylene-17β-3'-oxidoestra-4-ene
(E/Z)-3-(hydroxyimino)-6β-hydroxymethylene-17α-(1'-propenyl)-18-methyl-15β, 16β-methylene-17β-3'-oxidoestra-4-ene

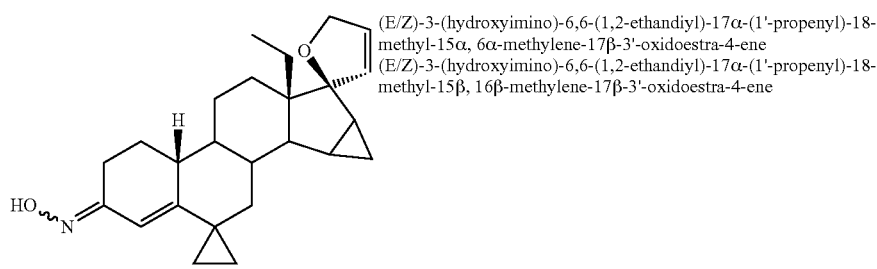

(E/Z)-3-(hydroxyimino)-6,6-(1,2-ethandiyl)-17α-(1'-propenyl)-18-methyl-15α, 6α-methylene-17β-3'-oxidoestra-4-ene
(E/Z)-3-(hydroxyimino)-6,6-(1,2-ethandiyl)-17α-(1'-propenyl)-18-methyl-15β, 16β-methylene-17β-3'-oxidoestra-4-ene

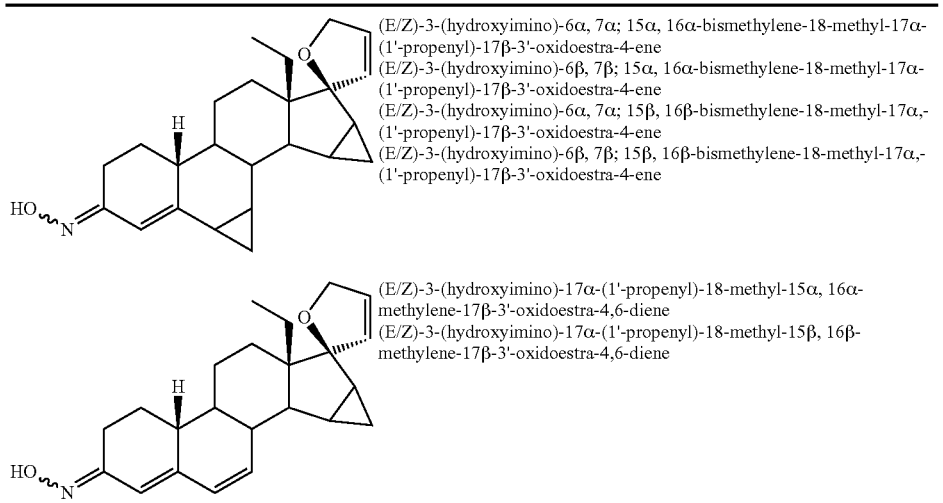

Owing to their progestational activity, the novel compounds with the general chemical formula I can be used alone or in combination with estrogen in drugs for contraception.

The derivatives according to the invention are thus suitable in particular for the production of a drug for oral contraception and for the treatment of pre-, peri- and postmenopausal problems, including use in preparations for hormone replacement therapy (HRT).

Because of their favorable activity profile, the derivatives according to the invention are also particularly well suited for the treatment of premenstrual problems, such as headaches, depressive moods, water retention and mastodynia.

Particularly preferable is the use of the derivatives according to the invention for the production of a drug with progestational, and preferably also antimineralcorticoid and neutral to slight androgenic action.

Treatment with the derivatives according to the invention preferably takes place in humans, but can also be performed in related mammalian species, such as for example in the dog and the cat.

For the use of the derivatives according to the invention as drugs, these are combined with least one suitable pharmaceutically harmless additive, for example a carrier. The additive is for example suitable for parenteral, preferably oral, administration. These are pharmaceutically suitable organic or inorganic additives, such as for example, water, gelatine, gum arabic, lactose, starch, magnesium stearate, talc, plant oils, polyalkylene glycols and the like. The drugs can be in solid form, for example as tablets, coated tablets, suppositories or capsules or in liquid form, for example as solutions, suspensions or emulsions. In addition, they optionally contain additives such as preservatives, stabilisers, wetting agents or emulsifiers, salts for modification of the osmotic pressure or buffers. For parenteral administration, oily solutions, such as for example solutions in sesame oil, castor oil and cottonseed oil, are particularly suitable. To increase the solubility, solubilizers, such as for example benzyl benzoate or benzyl alcohol, can be added. It is also possible to incorporate the derivatives according to the invention into a transdermal system and thereby to administer them transdermally. For oral administration, in particular tablets, coated tablets, capsules, pills, suspensions or solutions are options.

Further examples of administration routes are intravaginal or intrauterine administration. This is possible with physiologically tolerated solutions such as, for example, an aqueous or oily solution with or without suitable solubilizers, dispersants or emulsifiers. Examples of suitable oils are peanut oil, cottonseed oil, castor oil or sesame oil. The selection is by no means restricted thereto.

For intravaginal or intrauterine administration it is possible to use special systems such as an intravaginal system (e.g. vaginal ring, VRS) or an intrauterine system (IUS) which release an active substance of the present invention from a reservoir over a prolonged period (e.g. 1, 2, 3, 4 or 5 years).

A representative example of an intrauterine system which may be mentioned is MIRENAO®. This is a T-shaped, levonorgestrel-releasing intrauterine system from Bayer Schering Pharma AG.

Administration is further possible via an implanted depot system composed of an inert carrier material such as, for example, a biodegradable polymer or a synthetic silicone polymer. These depot systems release the active ingredient in a controlled manner over a prolonged period (e.g. 3 months to 3 years) and are implanted subcutaneously.

The dosage of the derivatives according to the invention in contraceptive preparations should be 0.01 to 10 mg per day. The daily dosage in the treatment of premenstrual problems is about 0.1 to 20 mg. The progestational preparations according to the invention in contraceptive preparations and in the drugs for the treatment of premenstrual problems are preferably administered orally. The daily dosage is preferably administered in a single dose. The aforementioned dosages relate to oral administration forms. On use of a depot formulation, the appropriate dosage, equivalent to the aforementioned oral dosages, is released continuously each day from the depot systems described above and employed in the long term.

A depot formulation, for example an IUS, releases per day an amount of 0.005 to 10 mg of a compound of general formula 1.

The progestational and estrogenic active substance components in contraceptive preparations are preferably orally administered together. The daily dosage is preferably administered in a single dose.

As estrogens, synthetic estrogens, preferably ethynylestradiol, but also Mestranol, and natural estrogens, including phytestrogens are options.

The estrogen is administered in a daily quantity which corresponds to the pharmacological action of 0.01 to 0.04 mg of ethynylestradiol. This amount relates to an oral administration form. If a different administration route is chosen, an appropriate dosage amount equivalent to the aforementioned oral dosage is to be used.

As estrogens in the drugs for the treatment of pre-, peri- and postmenopausal problems and for hormone replacement therapy, first and foremost natural estrogens are used, above all estradiol, but also the esters of estradiol, for example estradiol valerate, or else conjugated estrogens (CEEs=Conjugated Equine Estrogens).

The progestational, antimineralcorticoid and androgenic or anti-androgenic action of the compounds according to the invention was investigated by the following methods:

1. Progesterone Receptor Binding Test:

Using cytosol from progesterone receptor-expressing insect cells (Hi5), the competitive binding capacity to the progesterone receptor was determined via the ability to displace $^3$H-progesterone as the reference substance from the receptor. If a compound has an affinity corresponding to progesterone, this corresponds to the competition factor (CF) of 1. CF values greater than 1 are characterized by a lower affinity, and CF values less than 1 by a higher affinity, to the progesterone receptor.

2. Mineralocorticoid Receptor Binding Test:

The test was performed analogously to 1., with the following modifications: cytosol from mineralocorticoid receptor-expressing insect cells (Hi5) were used, and the reference substance was $^3$H-aldosterone.

3. Androgen Receptor Binding Test:

The test was performed analogously to 1., with the following modifications: cytosol from androgen receptor-expressing insect cells (Hi5) were used, and the reference substance was $^3$H-testosterone.

The results of the binding test and the ratio of the competition factors CF(PR) and CR(MR) are reproduced in Table 1, in which receptor binding values of drospirenone as reference substance A are also stated for comparison.

4. Determination of the Progestational Action by Means of Transactivation Tests:

For the culturing of the cells used for the assay, DMEM (Dulbecco's Modified Eagle Medium: 4500 mg/ml glucose; PAA, #E15-009) with 10% FCS (Biochrom, S0115, Lot #615B), 4 mM L-glutamine, 1% penicillin/streptomycin, 1 mg/ml G418 and 0.5 µg/ml puromycin was used as the culture medium.

Reporter cell lines (CHO K1 cells stably transfected with a fusion protein from the PR ligand binding domain and a Gal4 transactivation domain and a reporter construct which contained luciferase under the control of a Gal4-responsive promoter) were cultured at a density of $4\times10^4$ cells per well in white, opaque tissue culture plates each with 96 wells (PerkinElmer, #P12-106-017) and kept in culture medium containing 3% DCC-FCS (activated charcoal-treated serum, for removal of interfering components contained in the serum). The compounds to be tested were added eight hours later and the cells were incubated with the compounds for 16 hours. The experiments were performed three times. At the end of the incubation, the effector-containing medium was removed and replaced by lysis buffer. After addition of luciferase assay substrate (Promega, #E1501), the plates with the 96 wells were then introduced into a microplate luminometer (Pherastar, BMG labtech), and the luminescence was measured. The $IC_{50}$ values were evaluated using software for the calculation of dose-response relationships. Experimental results and corresponding results for drospirenone as reference substance A are reproduced in Table 2 for comparison.

5. Determination of the Antimineralocorticoid Action by Means of Transactivation Tests:

The determination of the antimineralocorticoid activity of the test substances was performed analogously to the transactivation tests described above.

The following modifications were made: here reporter cell lines were used (MDCK cells) which express the human mineralocorticoid receptor, and transiently contain a reporter construct which contains luciferase under the control of a steroid hormone-responsive promoter.

For culturing the cells used for the assay, DMEM EARLE'S MEM (PAA, Cat.: E15-025) stocked with 1000 penicillin/0.1 mg/ml streptomycin (PAA, Cat: P11-010), 4 mM L-glutamine (PAA, Cat: M11-004) and foetal calf serum (610 Witthaker, Cat: DE14-801F) was used as the culture medium.

For the determination of the antimineralocorticoid activity, 1 nM aldosterone (SIGMA A-6628, Lot 22H4033) was added to the cells in order to achieve almost maximal stimulation of the reporter gene. An inhibition of the effect indicated a mineralcorticoid-antagonistic action of the substances (Table 2; corresponding values for drospirenone (A) for comparison).

6. Determination of the Androgenic/Antiandrogenic Activity by Means of Transactivation Tests:

The determination of the androgenic/antiandrogenic activity of the test substances was performed analogously to the transactivation tests described above.

The following modifications were made: here reporter cell lines which express the androgen receptor (PC3 cells) and a reporter construct which contains luciferase under the control of a steroid hormone-responsive promoter were used.

For culturing the cells used for the assay, culture medium RPMI medium without phenol red (PAA, #E15-49), stocked with 100 U penicillin/0.1 mg/ml streptomycin (PAA, Cat: P11-010), 4 mM L-glutamine (PAA, Cat: M11-004) and foetal calf serum (B10 Witthaker, Cat: DE14-801F) was used.

For the determination of the antiandrogenic activity, 0.05 nM R1881 was added to the cells in order to achieve almost maximal stimulation of the reporter gene. An inhibition of the effect indicated an androgen-antagonistic action of the substances (Table 2; corresponding values for drospirenone (A) for comparison).

Insofar as the preparation of the starting compounds is not described, these are known to the person skilled in the art, or preparable analogously to known compounds or processes described here. The isomer mixtures can be separated into the individual compounds by normal methods, such as for example crystallisation, chromatography or salt formation. The preparation of the salts is effected in a normal way, by treating a solution of the compounds with the general chemical formula I with the equivalent quantity or an excess of a base or acid, which is optionally in solution, if necessary separating the precipitate or working up the solution in a normal way.

The preparation of the compounds with the general chemical formula I, starting from compounds with the general chemical formula I (Scheme 2), is effected by the processes stated in Scheme 1, in which $R^4$, $R^{6a}$, $R^{6b}$, $R^7$, $R^{18}$ and Z have the aforesaid meanings, and $R^6$, $R^7$ in 5 and 6 together comprise oxygen or a methylene group, U is oxygen, two alkoxy groups $OR^{19}$ or a $C_2$-$C_{10}$ alkylen-α, ω-dioxy group, which can be linear or branched, where $R^{19}$ stands for a $C_1$-$C_{20}$ alkyl residue, $R^{20}$ is a $C_1$-$C_{20}$ alkyl residue, X is an $NR^{21a}R^{21b}$ group or an alkoxy group $OR^{22}$, $R^{21a}$, $R^{21b}$ are each mutually independently selected from the group comprising hydrogen and $C_1$-$C_{10}$ alkyl, or together form a $C_4$-$C_{10}$ α,ω-alkylene group, which can be linear or branched and $R^{22}$ is a $C_1$-$C_{20}$ alkyl residue.

The compounds 2 and 3 in Scheme 1 each bear a double bond between $C^6$ and $C^6$ or between $C^5$ and $C^{10}$ and a further double bond between $C^2$ and $C^3$ or between $C^3$ and $C^4$.

The compounds 7 to 9 in Scheme 1 each bear a double bond between $C^4$ and $C^5$ or between $C^5$ and $C^6$ or between $C^5$ and $C^{10}$.

To the person skilled in the art, it is obvious that in the descriptions of the synthetic transformations it is always assumed that if necessary other functional groups present on the steroid skeleton are protected in suitable form.

The introduction of a 6,7 double bond with the formation of compounds with the general chemical formulae 4, 13 or 18 is effected via bromination of the respective 3,5 dienol ether 3, 12 or 17 followed by removal of hydrogen bromide (see for example J. Fried, J. A. Edwards, *Organic Reactions in Steroid Chemistry*, von Nostrand Reinhold Company 1972, S. 265-374).

The dienol ether bromination of the compounds 3, 12 or 17 can for example be effected analogously to the procedure from *Steroids* 1, 233 (1963). The hydrogen bromide removal with the formation of the compounds with the general chemical formulae 4, 13 or 18 is effected by heating the 6-bromo compound with basic reagents, such as for example LiBr or $Li_2CO_3$ in aprotic solvents such as dimethylformamide at temperatures of 50-120° C. or else by heating the 6-bromo compounds in a solvent such as collidine or lutidine.

The introduction of a substituent $R^4$ can for example be effected starting from a compound with the general chemical formulae 6, 11, 13, 14, 16 or 18 by epoxidation of the 4,5 double bond with hydrogen peroxide under alkaline conditions and reaction of the epoxides formed with acids with the general chemical formula H—$R^4$, where $R^4$ can be a halogen atom, preferably chlorine or bromine, in a suitable solvent. Compounds in which $R^4$ has the meaning bromine can for example be converted to compounds in which $R^4$ has the meaning fluorine with methyl 2,2-difluoro-2-(fluorosulfonyl)acetate in dimethylformamide in the presence of copper (I) iodide. Alternatively, starting from a compound with the general chemical formulae 6, 11, 13, 14, 16 or 18, halogen can be introduced directly by reaction with sulfuryl chloride or sulfuryl bromide in the presence of a suitable base, such as for example pyridine, with $R^4$ meaning chlorine or bromine.

Compound 4 is converted by methenylation of the 6,7 double bond by known processes, for example with dimethylsulfoxonium methylide (see for example DE-A 11 83 500, DE-A 29 22 500, EP-A 0 019 690, U.S. Pat. No. 4,291,029; *J. Am. Chem. Soc.* 84, 867 (1962)) into a compound 5 ($R^6$, $R^7$ together a methylene group), whereby a mixture of the α and β isomers is obtained, which can for example be separated into the individual isomers by chromatography.

Compounds of the type 5 can be obtained, as described in the examples or analogously to these procedures, with the use of reagents analogous to those described there.

The synthesis of the spirocyclic compound 18 ($R^{6a}$, $R^{6b}$ together comprise 1,2-ethanediyl) starts from compound 11 or 14, which is first converted into a 3-amino-3,5-diene derivative 15 (X=$NR^{21a}R^{21b}$). By reaction with formalin in alcoholic solution, the 6-hydroxymethylene derivative 16 ($R^6$=hydroxymethylene) is obtained. After conversion of the hydroxy group into a leaving group, such as for example a mesylate, tosylate or even benzoate, compound 18 can be prepared by reaction with trimethylsulfoxonium iodide with the use of bases such as for example alkali metal hydroxides or alkali metal alcoholates in suitable solvents, such as for example dimethyl sulfoxide.

For the introduction of a 6-methylene group, compound 16 ($R^6$=hydroxymethylene) can be dehydrated for example with hydrochloric acid in dioxan/water. Compound 18 ($R^{6a}$, $R^{6b}$ together methylene) can also be made after conversion of the hydroxy group into a leaving group, such as for example a mesylate, tosylate or even benzoate (see DE-A 34 02 329, EP-A 0 150 157, U.S. Pat. No. 4,584,288; *J. Med. Chem.* 34, 2464 (1991)).

A further possibility for the production of 6-methylene compounds 18 consists in the direct reaction of the 4(5) unsaturated 3-ketones, such as compound 16 ($R^6$=hydrogen), with acetals of formaldehyde in the presence of sodium acetate for example with phosphorus oxychloride or phosphorus pentachloride in suitable solvents, such as chloroform (see for example K. Annen, H. Hofmeister, H. Laurent and R. Wiechert, *Synthesis* 34 (1982)).

The 6-methylene compounds can be used for the preparation of compounds with the general chemical formula 18, in which $R^{6a}$ equals methyl and $R^{6b}$ and $R^7$ are omitted with the formation of a double bond between $C^6$ and $C^7$.

For this, for example a process described in *Tetrahedron* 21, 1619 (1965) can be used, in which an isomerization of the double bond is achieved heating of the 6-methylene compounds in ethanol with 5% palladium-charcoal catalyst, which has been pretreated either with hydrogen or by heating with a small quantity of cyclohexene. The isomerization can also be effected with a non-pretreated catalyst if a small quantity of cyclohexene is added to the reaction mixture. The formation of small proportions of hydrogenated products can be prevented by addition of an excess of sodium acetate.

Alternatively, the compound 17 (X=$OR^{22}$) can be used as a preliminary stage. The direct preparation of 6-methyl-4,6-dien-3-one derivatives has been described (see K. Annen, H. Hofmeister, H. Laurent and R. Wiechert, *Lieb. Ann.* 712 (1983)).

Compounds 18, in which $R^{6b}$ represents an α-methyl function, can under suitable conditions be prepared from the 6-methylene compounds (18: $R^{6a}$, $R^{6b}$ together methylene) by hydrogenation. The best results (selective hydrogenation of the exomethylene group) are achieved by transfer hydrogenation (*J. Chem. Soc.* 3578 (1954)). If the 6-methylene derivatives 18 are heated in a suitable solvent, such as for example ethanol, in the presence of a hydride donor, such as for example cyclohexene, then 6α-methyl derivatives are obtained in very good yields. Small proportions of 6β-methyl compound can be acid-isomerized (*Tetrahedron* 1619 (1965)).

The deliberate preparation of 6β-methyl compounds is also possible. For this, the 4-en-3-one; such as for example compound 16 are converted to the corresponding 3-ketals for example with ethylene glycol and trimethyl orthoformate in dichloromethane in the presence of catalytic quantities of an acid, for example p-toluenesulfonic acid. During this ketalization, the double bond in the position $C^5$ isomerizes. A selective epoxidation of this 5 double bond is effected for example by the use of organic peracids, for example m-chloroperbenzoic acid, in a suitable solvent, such as dichloromethane. Alternatively to this, the epoxidation can also be effected with hydrogen peroxide in the presence for example of hexachloroacetone or 3-nitrotrifluoroacetophenone. The 5,6α epoxides formed can then be opened axially by the use of appropriate alkylmagnesium halides or alkyllithium compounds. In this way, 5α-hydroxy-6β-alkyl compounds are obtained. The cleavage of the 3-keto protecting group can be effected while retaining the 5α-hydroxy function through treatment under mild acidic conditions (acetic acid or 4N hydrochloric acid at 0° C.). Basic elimination of the 5α-hydroxy function for example with dilute aqueous sodium hydroxide gives the 3-keto-4-ene compounds with a 6-alkyl group in the β position. Alternatively to this, the ketal cleavage under more drastic conditions (with aqueous hydrochloric acid or another strong acid) yields the corresponding 6α alkyl compounds.

The introduction of a 7-alkyl, 7-alkenyl or 7-alkynyl group with the formation of compounds with the general chemical formula 14 is effected by 1,6-addition of a corresponding organometallic compound to the preliminary stage with the general chemical formula 13 under the action of copper salts. Divalent metals such as magnesium and zinc are preferred, and chlorine, bromine and iodine are preferred as the counterion. Mono- or divalent copper compounds, such as for example copper chloride, copper bromide or copper acetate are suitable as copper salts. The reaction takes place in an inert solvent, such as for example tetrahydrofuran, diethyl ether or dichloromethane.

The compounds 6, 11, 13, 14, 16, 18 or 20 obtained, in which Z stands for an oxygen atom, can be converted into their corresponding E/Z-configured oximes or sulfonylhydrazones by reaction with hydroxylamine hydrochloride, alkyloxyamine hydrochlorides or sulfonylhydrazines in the presence of a tertiary amine at temperatures between –20 and +40° C. (general formula I with Z meaning NOR' or NNHSO$_2$R'). Suitable tertiary bases are for example trimethylamine, triethylamine, pyridine, N,N-dimethylaminopyridine, 1,5-diazabicyclo[4.3.0]non-5-ene (DBN) and 1,5-diazabicyclo[5.4.0]undec-5-ene (DBU), pyridine being preferable. An analogous process is for example described in WO 98/24801 A for the preparation of corresponding 3-oxyimino derivatives of drospirenone.

For the preparation of an end product with the general chemical formula I with Z meaning two hydrogen atoms, the 3-oxo group can for example be removed by the procedure stated in DE-A 28 05 490 by reductive cleavage of a thioketal of the 3-keto compound to a suitable preliminary stage, such as for example of compounds with one of the general chemical formulae 6, 11, 13, 14, 16, 18 or 20.

The formation of spiro ethers of compounds with one of the general chemical formulae 6 or 11 is effected, starting from the corresponding 17-hydroxypropenyl compounds 5 or 10, by conversion of the primary hydroxy group to a leaving group, followed by intramolecular substitution. Halogen atoms, such as for example chlorine, bromine or iodine, and also alkyl-, aryl- or aralkylsulfonates, such as for example methanesulfonate, phenylsulfonate, tolylsulfonate, trifluoromethanesulfonate and nonafluorobutanesulfonate are suitable as the leaving group. The intramolecular cyclization to the spiro ether can be effected by deprotonation of the tertiary hydroxy group with suitable bases, such as for example triethylamine, diethylamine, diisopropylethylamine, pyridine, dimethylaminopyridine, sodium hydride, sodium hexamethyldisilazane, potassium hexamethyldisilazane, potassium tert.-butanolate or n-butyllithium. Those methods and conditions which enable the introduction of the leaving group with direct intramolecular cyclization in one reaction vessel are preferred.

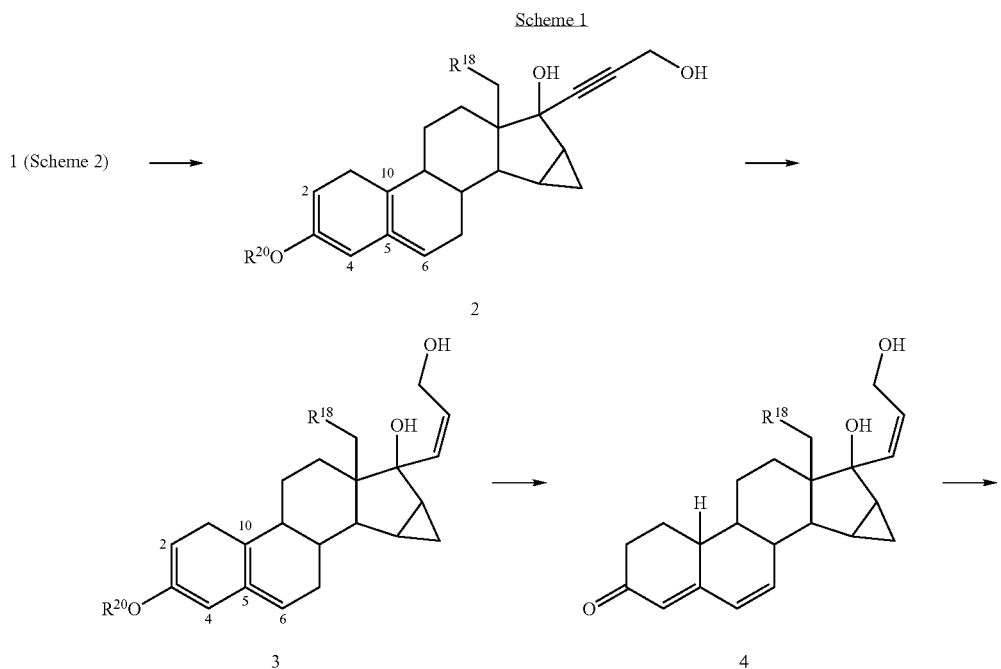

-continued
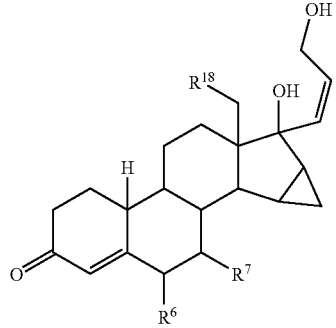 → 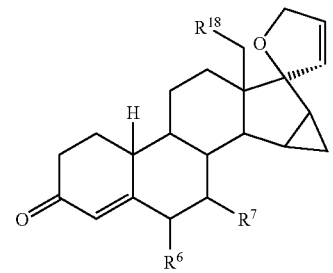
5 6
1 → 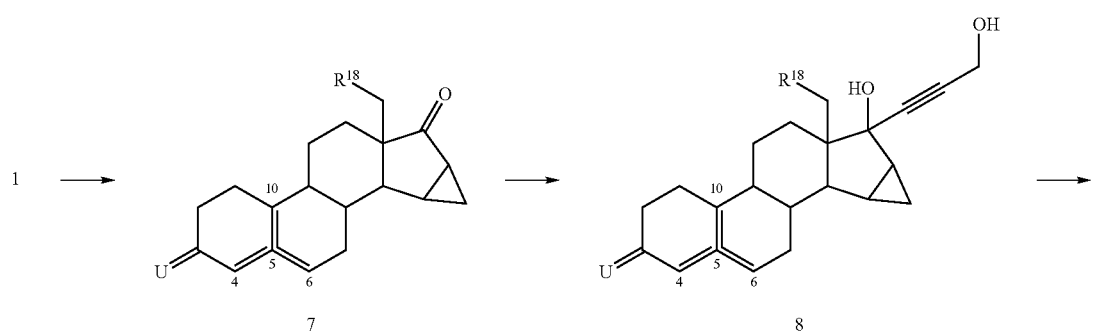
7 8
9
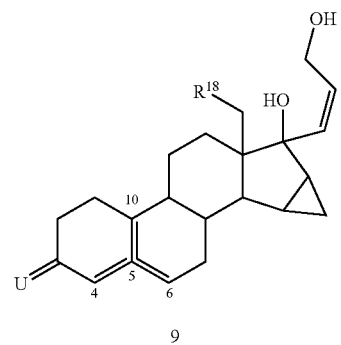
9 → 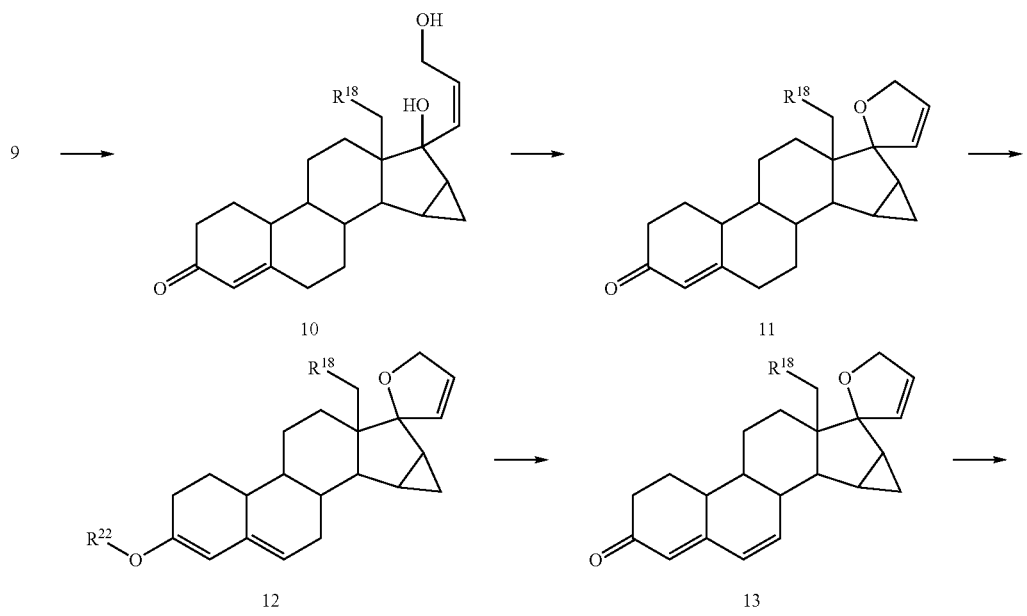
10 11
12 13

-continued
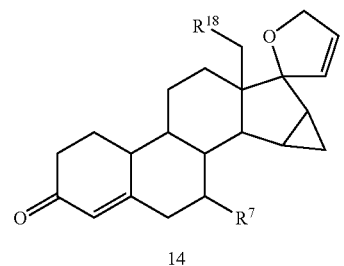
14
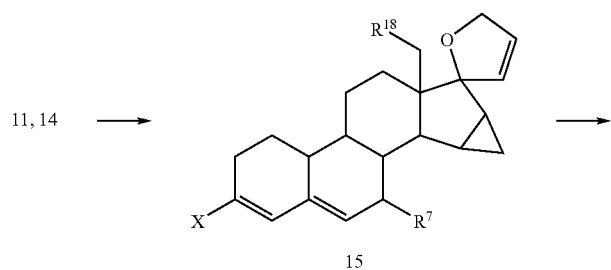
15
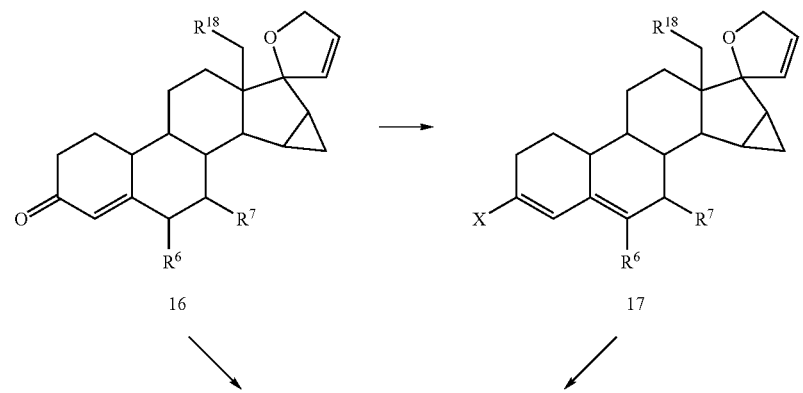
16 17

-continued
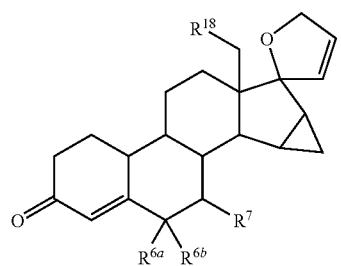
18
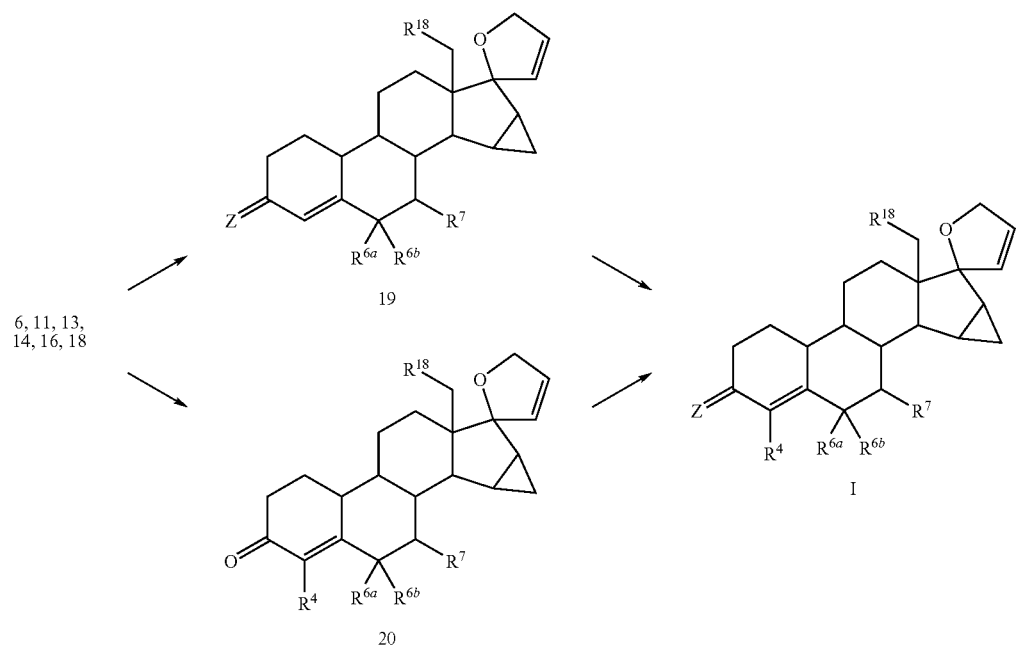
The compound 1 in Scheme 2 in each case bears a double bond between $C^5$ and $C^6$ or between $C^5$ and $C^{10}$ and a further double bond between $C^2$ and $C^3$ or between $C^3$ and $C^4$.
Scheme 2
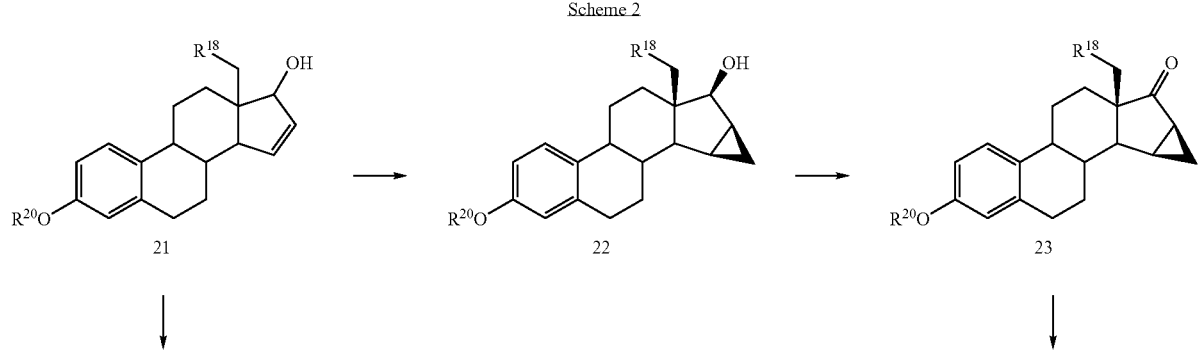

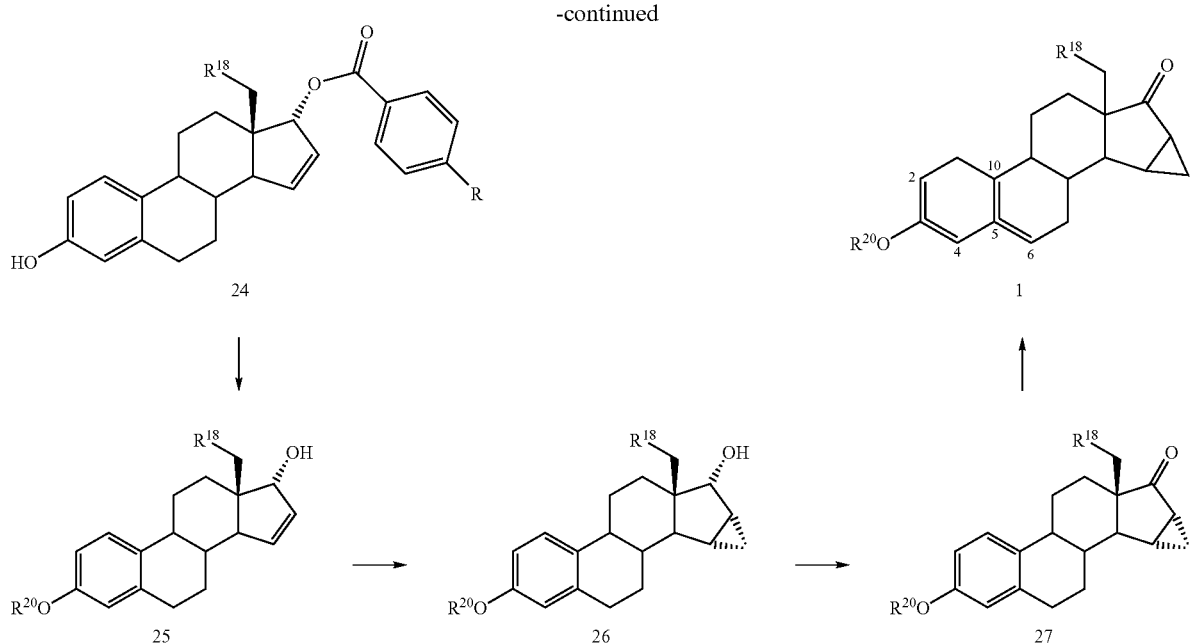

The following examples serve for the more detailed explanation of the invention, without limiting this to the examples presented:

EXAMPLE 1

Spiro Ether Formation

6β,7β;15β,16β-Bismethylene-18-methyl-17α-(1'-propenyl)-17β-3'-oxidoestra-4-en-3-one with water and saturated sodium chloride solution and dried over sodium sulfate. The residue obtained after filtration and solvent removal is purified by chromatography. 41.1 g of the title compound are isolated.

$^1$H-NMR (CDCl$_3$): δ=0.44 (1H), 0.57 (1H), 0.84 (3H), 0.89-1.02 (3H), 1.17-1.79 (12H), 1.87 (1H), 2.02-2.19 (2H), 2.29 (1H), 2.42 (1H), 4.55 (1H), 4.71 (1H), 5.81 (1H), 5.90 (1H), 6.11 (1H) ppm.

EXAMPLE 1a

Corey Cyclopropanation

6β,7β;15β,16β-Bismethylene-17α(Z)-(3'-hydroxypropen-1'-yl)-18-methyl-17β-hydroxyestra-4-en-3-one (A) and 6α,7α;15β,16β-bismethylene-17α(Z)-(3'-hydroxypropen-1'-yl)-18-methyl-17β-hydroxyestra-4-en-3-one (B)

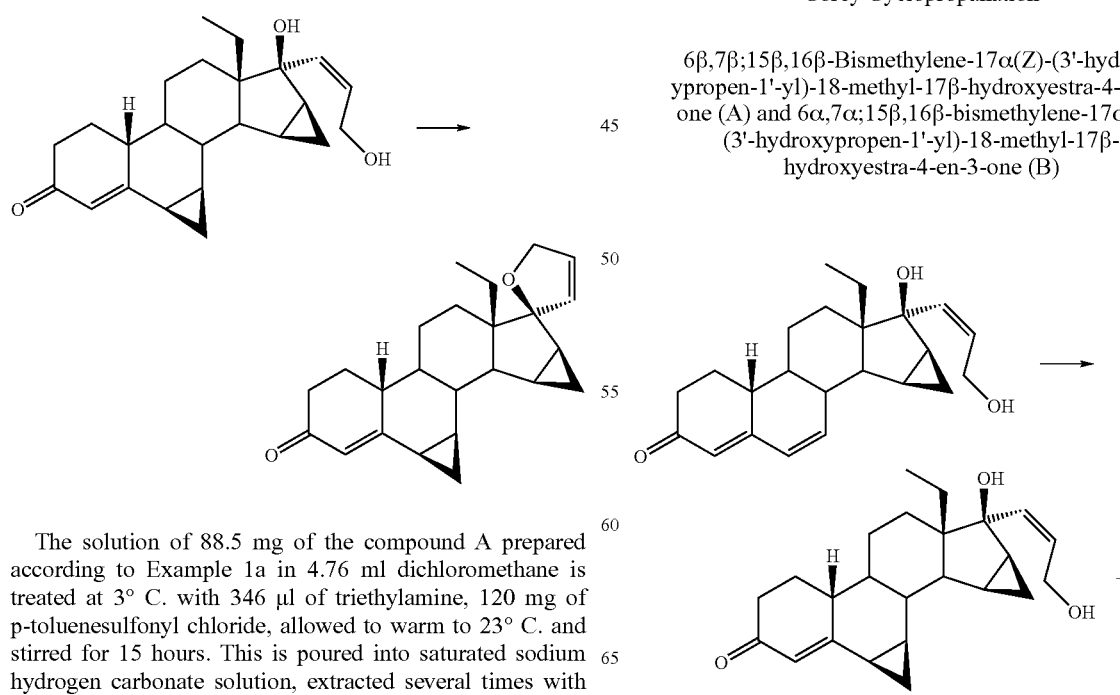

The solution of 88.5 mg of the compound A prepared according to Example 1a in 4.76 ml dichloromethane is treated at 3° C. with 346 μl of triethylamine, 120 mg of p-toluenesulfonyl chloride, allowed to warm to 23° C. and stirred for 15 hours. This is poured into saturated sodium hydrogen carbonate solution, extracted several times with ethyl acetate, and the combined organic extracts are washed -continued

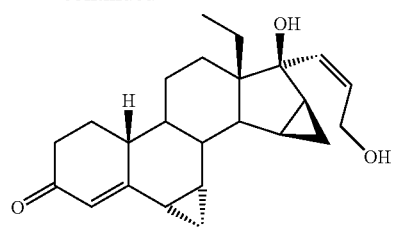

A solution of 16.8 g of sulfoxonium iodide in 373 ml dimethyl sulfoxide is treated portionwise at 23° C. with 3.33 g of a 55% suspension of sodium hydride in white oil. This is stirred for a further 2 hours, treated with 10.6 g of the compound prepared according to Example 1b and allowed to react for a further 2.5 hours. This is poured into water, extracted several times with ethyl acetate, and the combined organic extracts are washed with saturated sodium chloride solution and dried over sodium sulfate. The residue obtained after filtration and solvent removal is purified and separated by chromatography. 1.51 g of the title compound A and 1.01 g of the title compound B are isolated.

EXAMPLE 1b

Dienone Formation

17α(Z)-(3'-hydroxypropen-1'-yl)-18-methyl-15β,
16β-methylene-17β-hydroxyestra-4,6-dien-3-one

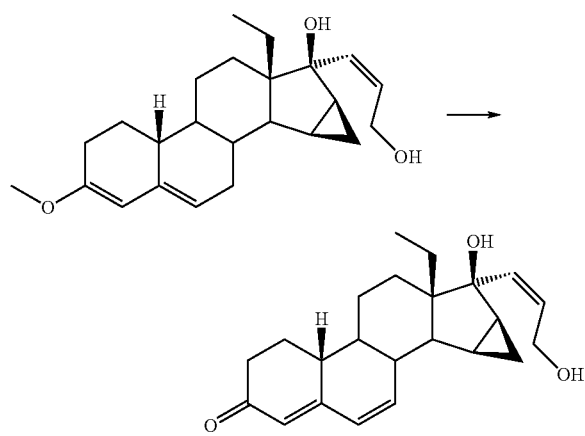

The solution of 10.4 of the compound prepared according to Example 1c in 125 ml dimethylformamide is treated at 3° C. with 1.03 g of sodium acetate, 10 ml of water and portionwise with a total of 4.23 g of dibromohydantoin. After 30 minutes, this is treated with 3.91 g of lithium bromide and 3.42 g of lithium carbonate and heated for 3 hours at a bath temperature of 100° C. This is poured into water and extracted several times with ethyl acetate. The combined organic extracts are washed with saturated sodium chloride solution and dried over sodium sulfate. The residue obtained after filtration and solvent removal is purified by chromatography. 6.35 g of the title compound are isolated.

EXAMPLE 1c

Lindlar Hydrogenation

17α(Z)-(3'-hydroxypropen-1'-yl)-3-methoxy-18-
methyl-15β,16β-methylene-17β-hydroxyestra-3,5-
diene

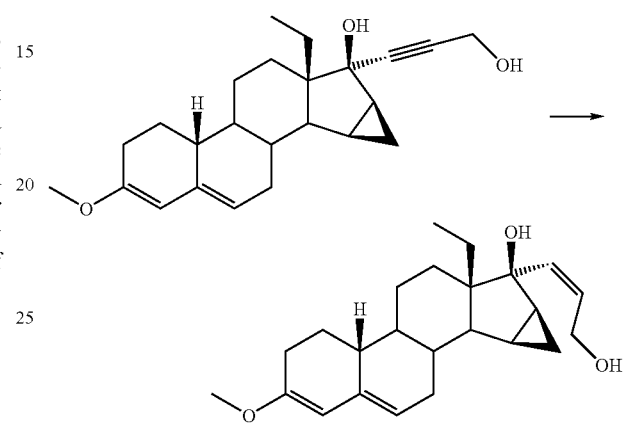

The solution of 75 g of the compound prepared according to Example 1d in 1.5 l tetrahydrofuran is treated with 100 ml of pyridine and 5 g of palladium on barium sulfate and hydrogenated at one atmosphere hydrogen. This is filtered over Celite and after concentration 75.7 g of the title compound are isolated, which are further reacted without purification.

EXAMPLE 1d

Hydroxypropyne Addition

17α(Z)-(3'-hydroxypropyn-1'-yl)-3-methoxy-18-
methyl-15β,16β-methylene-17β-hydroxyestra-3,5-
diene

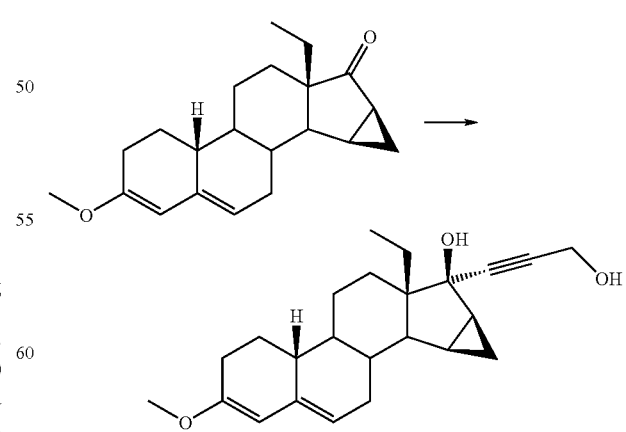

The solution of 83 ml of 2-propyn-1-ol in 1 l tetrahydrofuran is treated at −78° C. with 1 l of a 2.5 molar solution of butyllithium in hexane. After 30 minutes, the solution of 90 g of 3-methoxy-18-methyl-15β,16β-methylene-estra-3,5-dien-17-on in 0.5 l tetrahydrofuran is added dropwise, the mixture is allowed to warm to 23° C. and stirred for a further 3 hours. This is poured into saturated, ice-cold ammonium chloride solution, extracted several times with ethyl acetate, and the combined organic extracts are washed with saturated sodium chloride solution and dried over sodium sulfate. The residue obtained after filtration and solvent removal is purified by crystallisation. 90.3 g of the title compound are isolated.

EXAMPLE 2

6α,7α;15β,16β-Bismethylene-18-methyl-17α-(1'-propenyl)-17β-3'-oxidoestra-4-en-3-one

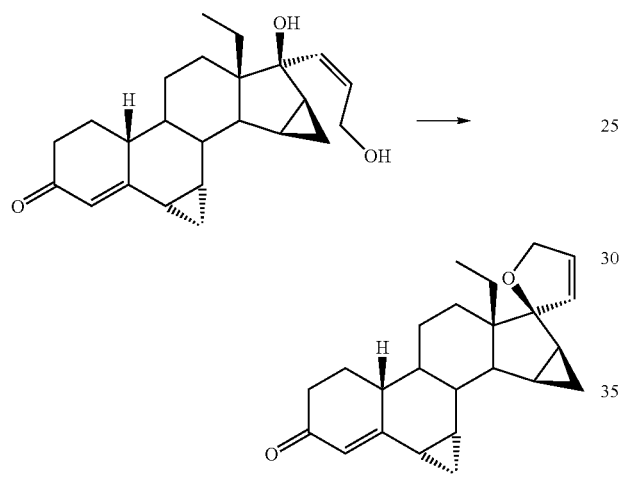

Analogously to Example 1, 114 mg of the compound B prepared according to Example 1a are reacted and after workup and purification 43 mg of the title compound are isolated.

$^1$H-NMR (CDCl$_3$): δ=0.42 (1H), 0.74-1.01 (5H), 0.86 (3H), 1.19 (1H), 1.26 (1H), 1.35-1.51 (3H), 1.60-1.92 (6H), 1.98-2.15 (3H), 2.26 (1H), 2.49 (1H), 4.56 (1H), 4.71 (1H), 5.82 (1H), 5.89 (1H), 6.04 (1H) ppm.

EXAMPLE 3

18-Methyl-15β,16β-methylene-17α-(1'-propenyl)-17β-3'-oxidoestra-4,6-dien-3-one

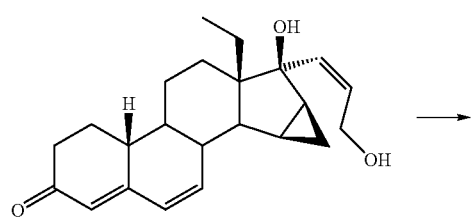

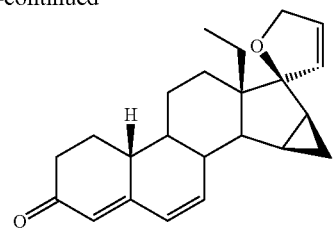

Analogously to Example 1, 4.67 g of the compound prepared according to Example 1a are reacted, and after workup and purification 3.66 g of the title compound are isolated.

$^1$H-NMR (CDCl$_3$): δ=0.51 (1H), 0.93 (3H), 1.01 (1H), 1.09-1.35 (4H), 1.42-1.64 (3H), 1.72-1.86 (3H), 2.00 (1H), 2.23-2.63 (5H), 4.21 (1H), 4.75 (1H), 5.84 (2H), 5.95 (1H), 6.30 (1H), 6.53 (1H) ppm.

EXAMPLE 4

1,6-Addition

7α,18-Bismethyl-15β,16β-methylene-17α-(1'-propenyl)-17β-3'-oxidoestra-4-en-3-one (A) and 7β,18-bismethyl-15β,16β-methylene-17α-(1'-propenyl)-17β-3'-oxidoestra-4-en-3-one (B)

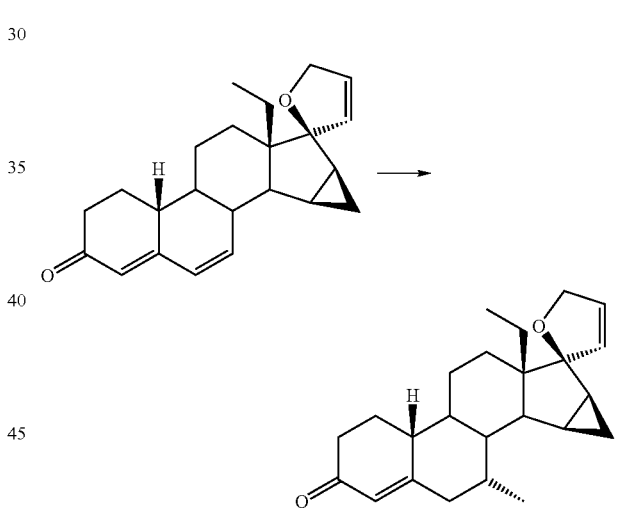

1.24 ml of a 3 molar solution of methylmagnesium chloride in tetrahydrofuran are added dropwise to the suspension of 30 mg of copper-(I) chloride in 5 ml tetrahydrofuran cooled to −30° C. and the mixture stirred a further 10 minutes. It is cooled to −25° C. and the solution is added dropwise to 500 mg of the compound prepared according to Example 3 in 5 ml tetrahydrofuran. After 1 minute, this is poured into 1N hydrochloric acid, extracted several times with ethyl acetate, and the combined organic extracts are washed with saturated sodium chloride solution and dried over sodium sulfate. The residue obtained after filtration and solvent removal is purified by chromatography. 267 mg of the title compound A are isolated as well as a still unpurified mixture, which contains quantities of the title compound B.

$^1$H-NMR (CDCl$_3$) of A: δ=0.87 (3H), 0.88 (3H), 0.90 (1H), 1.03 (1H), 1.11-1.30 (4H), 1.43-1.89 (8H), 2.05 (1H), 2.20-2.44 (5H), 2.55 (1H), 4.56 (1H), 4.71 (1H), 5.81 (1H), 5.85 (1H), 5.89 (1H) ppm.

EXAMPLE 5

7α-Ethyl-18-methyl-15β,16β-methylene-17α-(1'-propenyl)-17β-3'-oxidoestra-4-en-3-one (A) and
7β-ethyl-18-methyl-15β,16β-methylene-17α-(1'-propenyl)-17β-3'-oxidoestra-4-en-3-one (B)

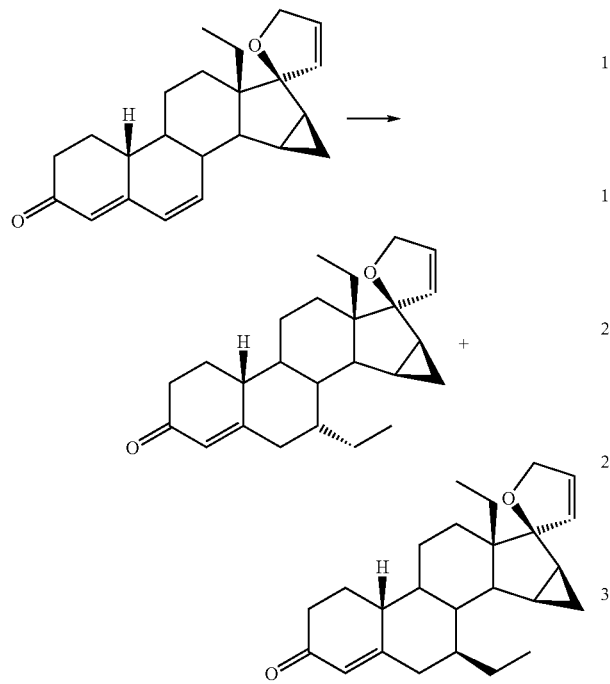

Analogously to Example 4, 300 mg of the compound prepared according to Example 3 are reacted using ethylmagnesium chloride, and after workup and purification 26 mg of the title compound A and 26 mg of the title compound B are isolated.

$^1$H-NMR (CDCl$_3$) of A: δ=0.40 (1H), 0.87 (3H), 0.90 (1H), 0.93 (3H), 1.01 (1H), 1.06-1.17 (3H), 1.20-1.26 (2H), 1.42-1.54 (3H), 1.66 (1H), 1.71 (1H), 1.79 (1H), 1.86 (1H), 1.90 (1H), 1.95 (1H), 2.06 (1H), 2.22-2.29 (2H), 2.35-2.43 (2H), 2.60 (1H), 4.56 (1H), 4.70 (1H), 5.81 (1H), 5.86 (1H), 5.89 (1H) ppm.

$^1$H-NMR (CDCl$_3$) of B: δ=0.45 (1H), 0.89 (3H), 0.93-1.24 (5H), 0.98 (3H), 1.33-1.89 (9H), 1.96 (1H), 2.02-2.38 (6H), 2.64 (1H), 4.56 (1H), 4.67 (1H), 5.81 (1H), 5.84 (1H), 5.91 (1H) ppm.

EXAMPLE 6

7α-Vinyl-18-methyl-15β,16β-methylene-17α-(1'-propenyl)-17β-3'-oxidoestra-4-en-3-one (A) and
7β-vinyl-18-methyl-15β,16β-methylene-17α-(1'-propenyl)-17β-3'-oxidoestra-4-en-3-one (B)

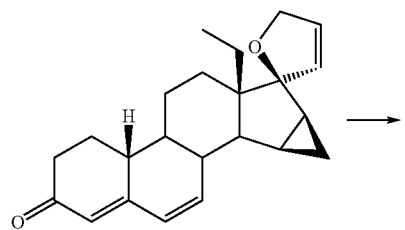

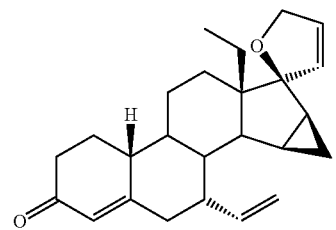

Analogously to Example 4, 200 mg of the compound prepared according to Example 3 are reacted using vinylmagnesium chloride, and after workup and purification 32 mg of the title compound A are isolated, as well as a still unpurified mixture which contains quantities of the title compound B.

$^1$H-NMR (CDCl$_3$) of A: δ=0.39 (1H), 0.89 (3H), 0.98 (1H), 1.04-1.33 (4H), 1.37-1.61 (3H), 1.65-1.99 (5H), 2.10-2.43 (4H), 2.54 (1H), 2.69 (1H), 2.85 (1H), 4.55 (1H), 4.67 (1H), 5.17 (1H), 5.22 (1H), 5.81-6.01 (4H) ppm.

EXAMPLE 7

7α-Cyclopropyl-18-methyl-15β,16β-methylene-17α-(1'-propenyl)-17β-3'-oxidoestra-4-en-3-one (A) and 7β-cyclopropyl-18-methyl-15α,16β-methylene-17α-(1'-propenyl)-17β-3'-oxidoestra-4-en-3-one (B)

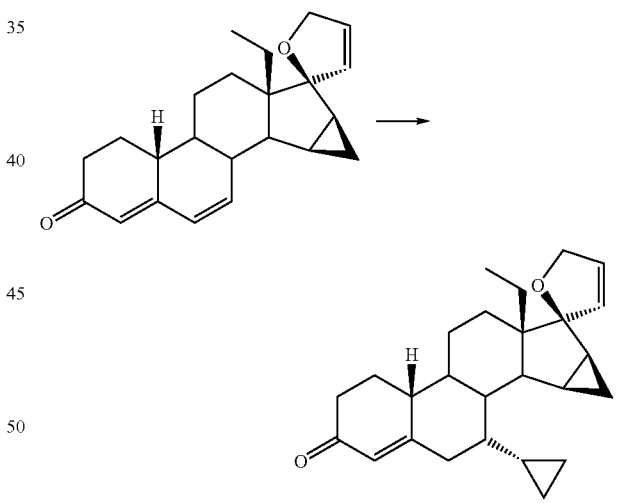

Analogously to Example 4, 200 mg of the compound prepared according to Example 3 are reacted using cyclopropylmagnesium bromide, and after workup and purification 17 mg of the title compound A are isolated, as well as a still unpurified mixture which contains quantities of the title compound B.

$^1$H-NMR (CDCl$_3$) of A: δ=0.11 (1H), 0.31-0.75 (5H), 0.90 (3H), 0.96-1.25 (4H), 1.38-1.77 (8H), 1.84-2.03 (2H), 2.11-2.57 (6H), 4.57 (1H), 4.69 (1H), 5.84-5.97 (3H) ppm.

EXAMPLE 8

15β,16β-Methylene-17α-(1'-propenyl)-17β-3'-oxi-doestra-4-en-3-one

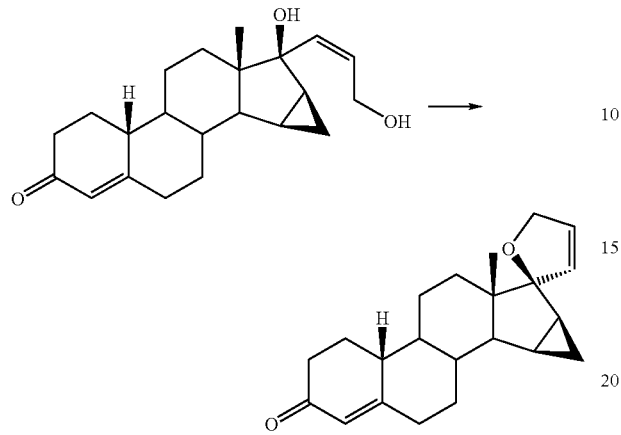

Analogously to Example 1, 5 g of the compound prepared according to Example 8a are reacted, and after workup and purification 3.37 g of the title compound are isolated.

$^1$H-NMR (CD2Cl2): δ=0.31 (1H), 0.84 (1H), 0.97 (3H), 1.05-1.32 (7H), 1.58 (2H), 1.65 (1H), 1.76 (1H), 2.03-2.41 (6H), 2.52 (1H), 4.52 (1H), 4.61 (1H), 5.77 (1H), 5.81 (1H), 5.89 (1H) ppm.

EXAMPLE 8a

Enone Formation from Dienol Ethers with Oxalic Acid

17α(Z)-(3'-hydroxypropen-1'-yl)-15β,18β-methylene-17β-hydroxyestra-4-en-3-one

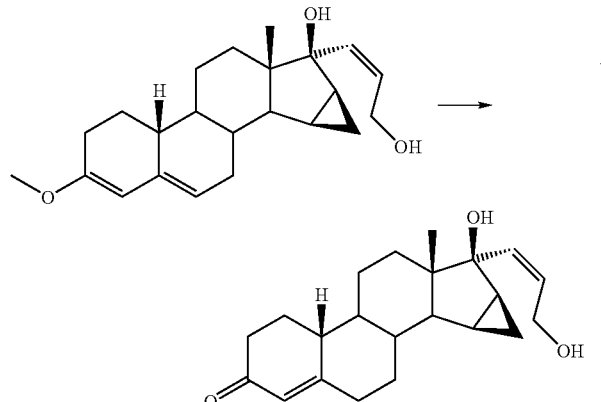

The suspension of 5.0 g of the compound prepared according to Example 8b in 30 ml acetone and 30 ml water is treated with 50 ml of a saturated aqueous solution of oxalic acid, 30 ml of methanol and 50 ml of tetrahydrofuran are added and the mixture stirred for 5 hours at 23° C. This is poured into saturated sodium hydrogen carbonate solution, extracted several times with ethyl acetate, and the combined organic extracts are washed with saturated sodium chloride solution and dried over sodium sulfate. The residue obtained after filtration and solvent removal is purified by chromatography. 4.26 g of the title compound are isolated.

EXAMPLE 8b

17α(Z)-(3'-hydroxypropen-1'-yl)-3-methoxy-15β,16β-methylene-17β-hydroxyestra-3,5-diene

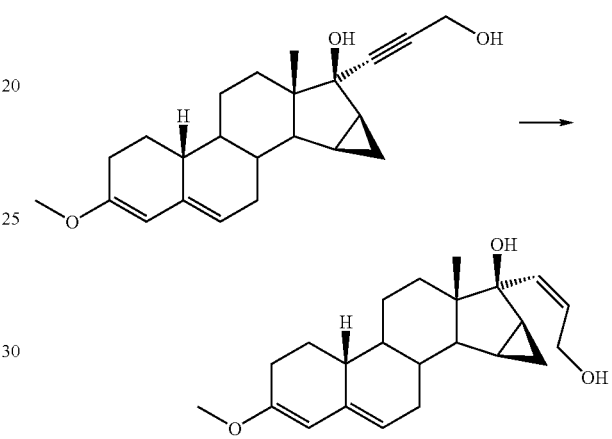

Analogously to Example 1c, 23.8 g of the compound prepared according to Example 8c are reacted, and after workup and purification 23.7 g of the title compound are isolated.

EXAMPLE 8c

17α(Z)-(3'-hydroxypropyn-1'-yl)-3-methoxy-15β,16β-methylene-17β-hydroxyestra-3,5-diene

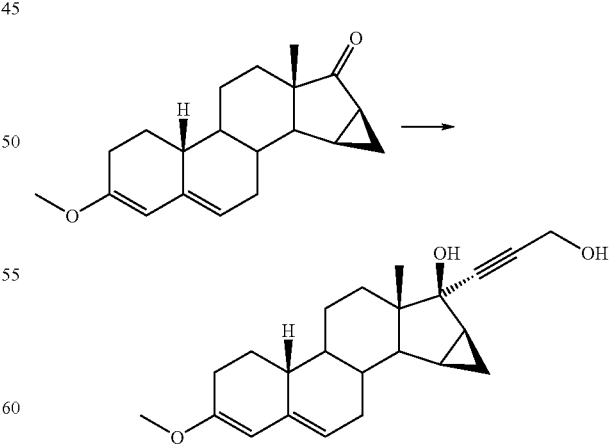

Analogously to Example 1d, 38 g of 3-methoxy-15β,16β-methylene-estra-3,5-dien-17-one are reacted, and after workup and purification 39.2 g of the title compound are isolated.

EXAMPLE 9

6-Hydroxymethyl Addition

6β-Hydroxymethylene-18-methyl-15β,16β-methylene-17α-(1'-propenyl)-17β-3'-oxidoestra-4-en-3-one

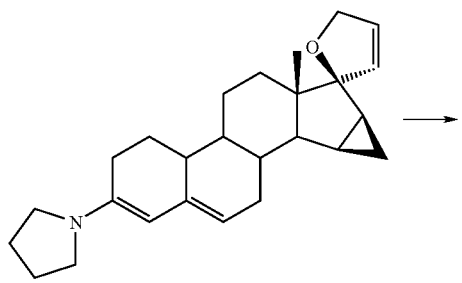

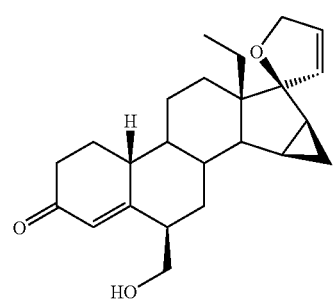

The solution of 322 mg of the compound prepared according to Example 9a in a mixture of 3 ml toluene and 7 ml ethanol is treated with 323 µl of a 37% aqueous formaldehyde solution and stirred for 15 hours at 23° C. This is concentrated and the residue purified by chromatography. 80 mg of the title compound are isolated.

$^1$H-NMR (CDCl$_3$): δ=0.38 (1H), 0.89 (3H), 0.92-1.23 (5H), 1.33 (1H), 1.40-1.85 (9H), 2.13 (1H), 2.18-2.33 (3H), 2.40 (1H), 2.71 (1H), 3.75 (2H), 4.56 (1H), 4.68 (1H), 5.85 (1H), 5.91 (1H), 5.92 (1H) ppm.

EXAMPLE 9a

Dienamine for 6-Alkylation

18-Methyl-15β,16β-methylene-3-pyrrolidinyl-17α-(1'-propenyl)-17β-3'-oxidoestra-3,5-diene

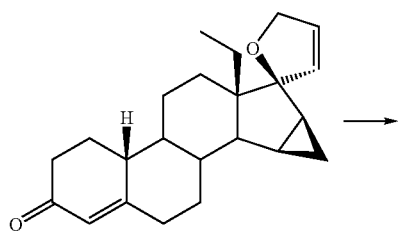

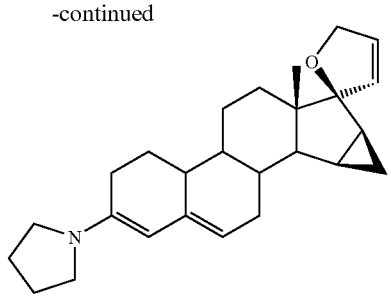

The solution of 500 mg of the compound prepared according to Example 8 in 5 ml methanol is treated with 282 µl of pyrrolidine and heated for 2 hours under reflux. This is cooled, the precipitate filtered off at the pump, then washed with a little cold methanol and 329 mg of the title compound are obtained, which is reacted further without additional purification.

EXAMPLE 10

6-Spirocyclopropanation 6,6-(1,2-Ethanediyl)-18-methyl-15β,16β-methylene-17α-(1'-propenyl)-17β-3'-oxidoestra-4-en-3-one

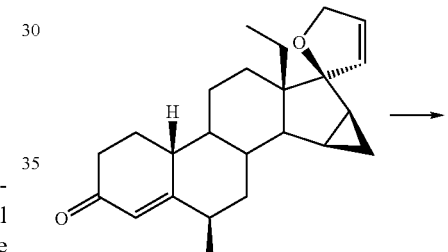

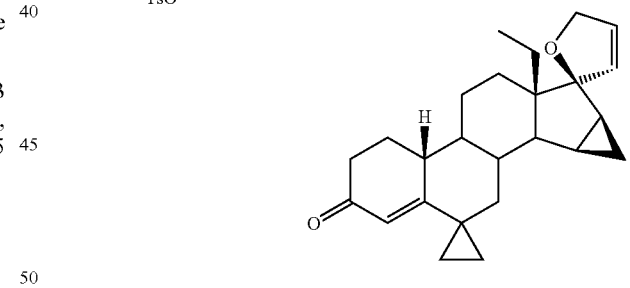

98 mg of trimethylsulfoxonium iodide are dissolved in 1.9 ml of dimethyl sulfoxide, treated with 17.8 mg of a 60% sodium hydride dispersion and stirred for 2 hours at 23° C. Next, the solution of 58 mg of the compound prepared according to Example 10a is added dropwise to 0.76 ml of dimethyl sulfoxide and stirred for a further 2 hours at 23° C. This is poured into water, extracted several times with ethyl acetate, and the combined organic extracts are washed with water and saturated sodium chloride solution and dried over sodium sulfate. The residue obtained after filtration and solvent removal is purified by chromatography. 15 mg of the title compound are isolated.

$^1$H-NMR (CDCl$_3$): δ=0.35 (1H), 0.45 (1H), 0.62 (1H), 0.83 (1H), 0.91 (3H), 0.95-1.35 (8H), 1.43-1.88 (7H), 1.95 (1H), 2.15-2.42 (4H), 4.56 (1H), 4.67 (1H), 5.68 (1H), 5.86 (1H), 5.92 (1H) ppm.

EXAMPLE 10a

6-Tosyloxymethyl

18-Methyl-15β,16β-methylene-6β-(p-tolylsulfonyloxymethyl)-17α-(1'-propenyl)-17β-3'-oxidoestra-4-en-3-one

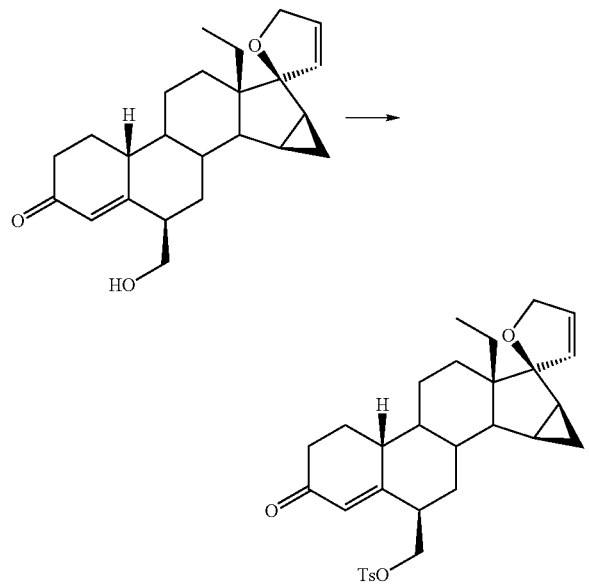

The solution of 245 mg of the compound prepared according to Example 9 in 11 ml dichloromethane is treated with 1.1 ml of triethylamine and 395 mg of p-tolueneulphonyl chloride and stirred for 15 hours at 23° C. This is poured into saturated sodium carbonate solution, extracted several times with ethyl acetate, and the combined organic extracts are washed with water and saturated sodium chloride solution and dried over sodium sulfate. The residue obtained after filtration and solvent removal is purified by chromatography. 58 mg of the title compound are isolated.

EXAMPLE 11

15β,16β-Methylene-17α-(1'-propenyl)-17β-3'-oxidoestra-4,6-dien-3-one

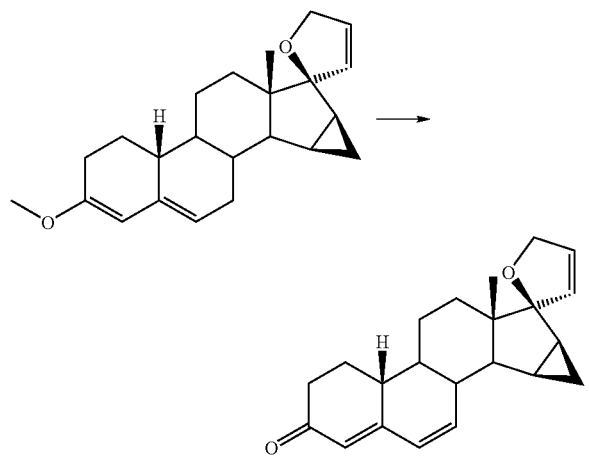

Analogously to Example 1b, 2.5 g of the compound prepared according to Example 11a are reacted, and after workup and purification 884 mg of the title compound are isolated.

$^1$H-NMR (CDCl$_3$): δ=0.44 (1H), 1.04 (3H), 1.11-1.61 (8H), 1.74-1.88 (2H), 2.22-2.55 (5H), 4.57 (1H), 4.67 (1H), 5.78 (1H), 5.86 (1H), 5.95 (1H), 6.30 (1H), 6.53 (1H) ppm.

EXAMPLE 11a

Dienol Ether Formation

15β,16β-Methylene-17α-(1'-propenyl)-17β-3'-oxidoestra-4,6-dien-3-one

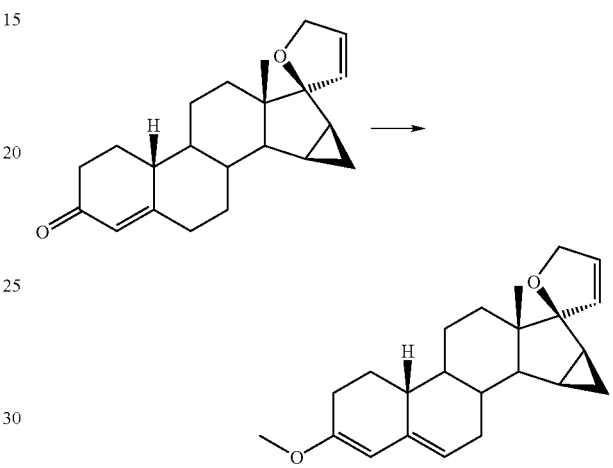

The solution of 2.5 g of the compound prepared according to Example 8 in 35 ml 2,2-dimethoxypropane is treated with 290 mg of pyridinium p-toluenesulfonate and heated for 3 hours under reflux. This is poured into saturated sodium hydrogen carbonate solution, extracted several times with ethyl acetate, and the combined organic extracts are washed with saturated sodium chloride solution and dried over sodium sulfate. The residue obtained after filtration and solvent removal is further reacted without purification. 2.8 g of the title compound are isolated.

EXAMPLE 12

17α-(1'-propenyl)-15α,16α-methylene-17β-3'-oxidoestra-4-en-3-one

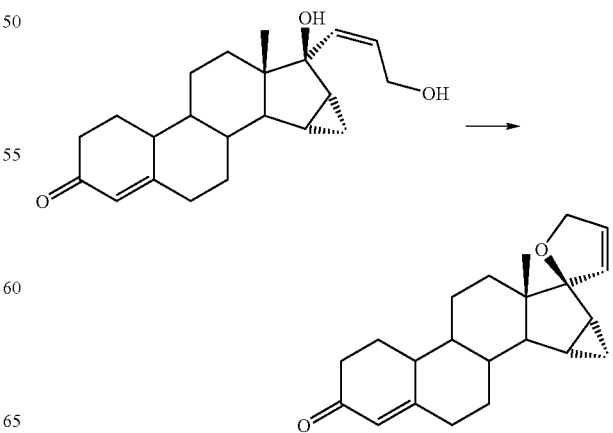

Analogously to Example 1, 2.5 g of the compound prepared according to Example 12a are reacted, and after workup and purification 1.66 g of the title compound are isolated.

$^1$H-NMR (CDCl$_3$): δ 0.56-0.68 (2H), 0.77 (1H), 0.97 (1H), 1.06-1.39 (5H), 1.24 (3H), 1.49-1.68 (3H), 1.77 (1H), 2.09-2.48 (6H), 2.56 (1H), 4.61 (1H), 4.70 (1H), 5.75 (1H), 5.88 (1H), 5.95 (1H) ppm.

EXAMPLE 12a

17α(Z)-(3'-hydroxypropen-1'-yl)-15α,16α-methylene-17β-hydroxyestra-4-en-3-one

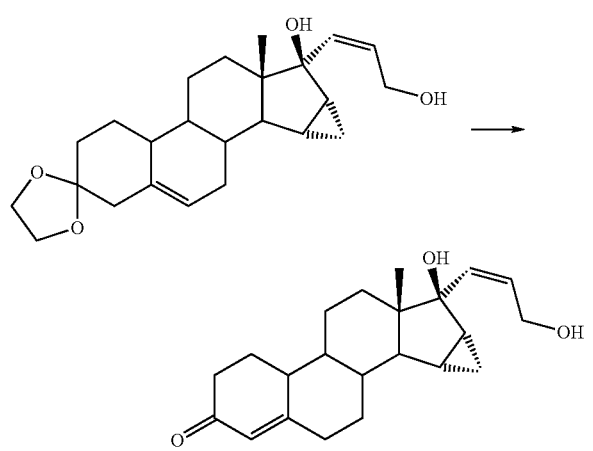

The solution of 300 mg of the compound prepared according to Example 12b in 15 ml acetone is treated with 0.83 ml of a 4N hydrochloric acid and stirred for 1 hour at 23° C. This is poured into saturated sodium hydrogen carbonate solution, extracted several times with ethyl acetate, and the combined organic extracts are washed with saturated sodium chloride solution and dried over sodium sulfate. The residue obtained after filtration and solvent removal is purified by chromatography. 135 mg of the title compound are isolated.

EXAMPLE 12b

17α(Z)-(3'-hydroxypropen-1'-yl)-15α,16α-methylene-17β-hydroxyestra-5-en-3-one-3-ethylene ketal and 17α(Z)-(3'-hydroxypropen-1'-yl)-15α,16α-methylene-17β-hydroxyestra-5(10)-en-3-one-3-ethylene ketal

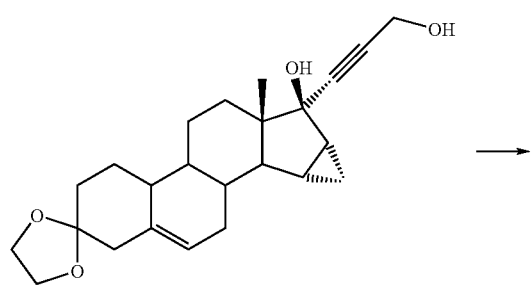

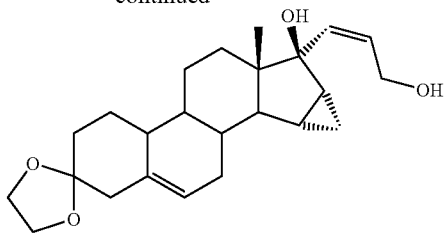

Analogously to Example 1c, 300 mg of the compound prepared according to Example 12c are reacted, and after workup 300 mg of the title compound are isolated, which are further reacted without purification.

EXAMPLE 12c

17α(Z)-(3'-hydroxypropyn-1'-yl)-15α,16α-methylene-17β-hydroxyestra-5-en-3-one-3-ethylene ketal and 17α(Z)-(3'-hydroxypropyn-1'-yl)-15α,16α-methylene-17β-hydroxyestra-5(10)-en-3-one-3-ethylene ketal Analogously to Example 1d, 278 mg of the compound prepared according to Example 12d are reacted, and after workup 347 mg of the title compound are isolated, which are further reacted without purification.

EXAMPLE 12d

15α,16α-Methylene-estra-5-en-3,17-dion-3-ethylene ketal and 15α,16α-methylene-estra-5(10)-en-3,17-dion-3-ethylene ketal

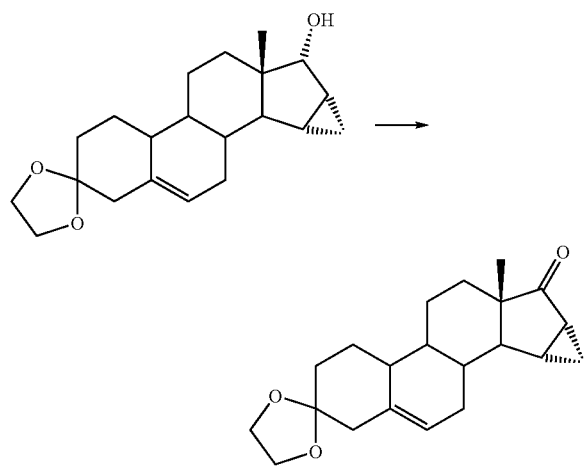

The solution of 1.06 g of the compound prepared according to Example 12e in 32 ml dichloromethane is treated with one spatula tip of molecular sieve 4 Å, 700 mg of N-methylmorpholino-N-oxide and 90 mg of tetrabutylammonium perruthenate and stirred at 23° C. for ca. 16 hours. This is concentrated and the residue purified by chromatography. 878 mg of the title compounds are isolated.

EXAMPLE 12e

15α,16α-Methylene-17α-hydroxyestra-5-en-3-one-3-ethylene ketal and 15α,16α-methylene-17α-hydroxyestra-5(10)-en-3-one-3-ethylene ketal

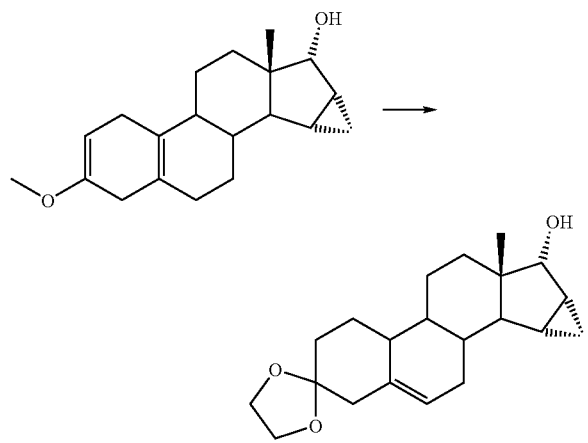

The solution of 500 mg of the compound prepared according to Example 12f in 10 ml tetrahydrofuran is treated with 10 ml of ethylene glycol and 4.4 mg of p-toluene-sulfonic acid hydrate and stirred at 23° C. for 2 hours. This is poured into saturated sodium hydrogen carbonate solution, extracted several times with ethyl acetate, and the combined organic extracts are washed with saturated sodium chloride solution and dried over sodium sulfate. The residue obtained after filtration and solvent removal is purified by chromatography. 359 mg of the title compound are isolated.

EXAMPLE 12f

3-Methoxy-15α,16α-methylene-17α-hydroxyestra-2,5(10)-diene

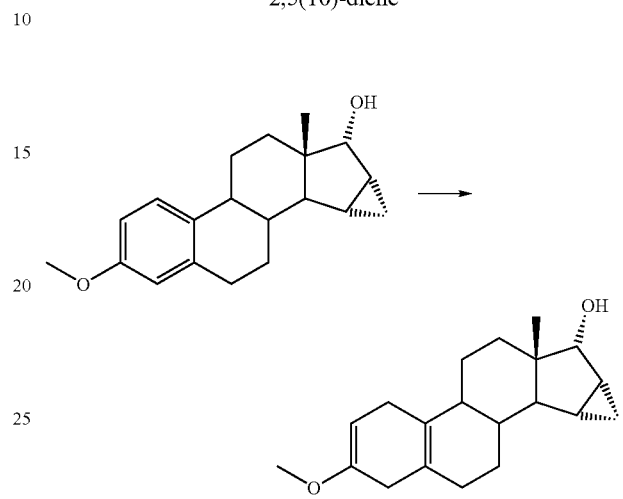

597 ml of ammonia are treated with 9.91 g of lithium at −75° C. and the solution of 24.6 g of the compound prepared according to Example 12g in 1.2 l tetrahydrofuran added dropwise within 1 hour. This is treated with 720 ml of ethanol, allowed to warm to −50° C. after 1 hour, and stirred for a further 2 hours. Next, it is treated with 600 ml water, allowed to warm to 23° C., extracted several times with ethyl acetate, and the combined organic extracts are washed with saturated sodium chloride solution and dried over sodium sulfate. After filtration and solvent removal, 27.1 g of the title compound is isolated, which is further reacted without purification.

EXAMPLE 12g

3-Methoxy-15α,16α-methylene-17α-hydroxyestra-1,3,5(10)-triene

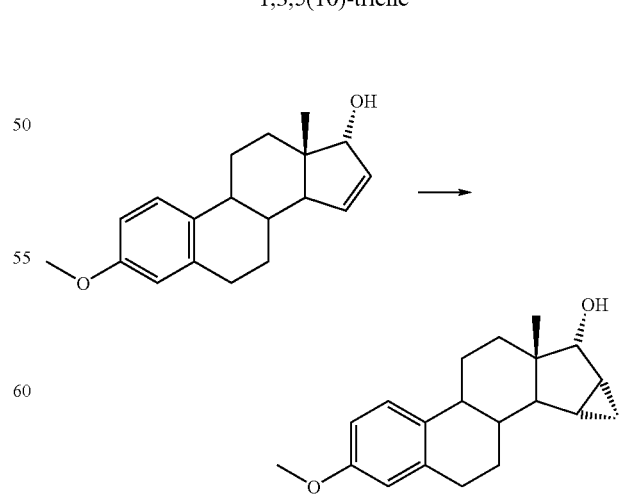

A suspension of 1.5 g of copper(II) acetate in 900 ml diethyl ether is treated with 86.6 g of zinc dust and heated for 10 minutes under reflux. Next, this is treated with 11.7 ml of diiodomethane and heated for a further 30 minutes under reflux. The solution of 37.6 g of the compound prepared according to Example 12h in 100 ml tetrahydrofuran is added, as well as a further 35 ml of diiodomethane in total divided over 40 hours. The cooled mixture is filtered over Celite, and the filtrate is washed with saturated sodium chloride solution and dried over sodium sulfate. The residue obtained after filtration and solvent removal is purified by recrystallisation. 24.6 g of the title compound are isolated.

EXAMPLE 12h

3-Methoxy-17α-hydroxyestra-1,3,5(10), 15-tetraene

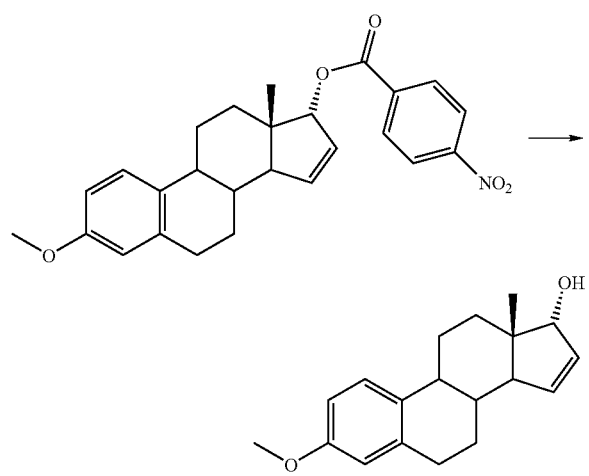

The solution of 96.3 g of the compound prepared according to Example 12i in 1.1 l methanol is treated with 75.5 g of potassium carbonate and stirred at 50° C. for 2 hours. This is concentrated, treated with water, extracted several times with ethyl acetate, and the combined organic extracts are washed with water and dried over sodium sulfate. The residue obtained after filtration and solvent removal is purified by recrystallisation. 46 g of the title compound are isolated.

EXAMPLE 12i

3-Methoxy-estra-1,3,5(10),15-tetraen-17-yl 4-nitrobenzoate

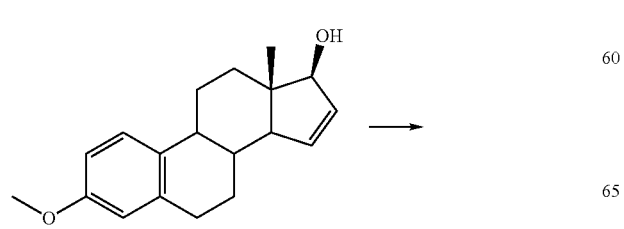

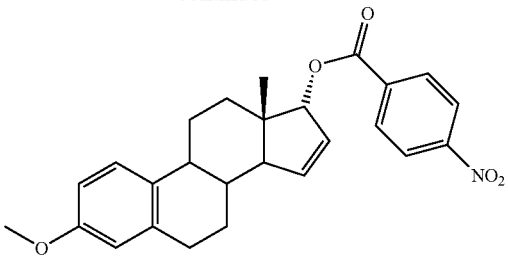

The solution of 43.9 g of 3-methoxy-17β-hydroxyestra-1,3,5(10),15-tetraene in 1.6 l tetrahydrofuran is treated with 121 g of triphenylphosphine, 27.1 g of 4-nitrobenzoic acid and 30.9 ml of diisopropyl azodicarboxylate and stirred at 23° C. for 2 hours. This is treated with saturated sodium chloride solution, extracted with ethyl acetate, and the combined organic extracts are washed with saturated sodium chloride solution and dried over sodium sulfate. The residue obtained after filtration and solvent removal is taken up 1.2 l acetone, treated with 80 ml of a 30% hydrogen peroxide solution with cooling, and after 20 minutes poured with cooling into 600 ml of a semi-concentrated sodium thiosulfate solution. This is extracted with ethyl acetate, and the combined organic extracts are washed with saturated sodium chloride solution and dried over sodium sulfate. The residue obtained after filtration and solvent removal is purified by recrystallisation. 52.5 g of the title compound are isolated.

EXAMPLE 13

17α-(1-Propenyl)-15α,16α-methylene-17β-3'-oxi-doestra-4,6-dien-3-one

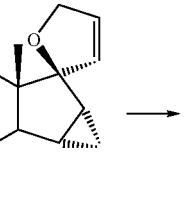

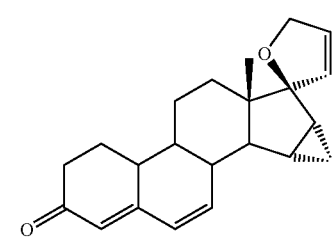

Analogously to Example 1b, 1.13 g of the compound prepared according to Example 13a are reacted, and after workup and purification 1.03 g of the title compound are isolated.

$^{1}$H-NMR (CD$_2$Cl$_2$): δ=0.60 (1H), 0.75 (1H), 0.90-1.74 (9H), 1.19 (3H), 2.19-2.50 (5H), 4.52 (1H), 4.62 (1H), 5.70 (1H), 5.72 (1H), 5.92 (1H), 6.23 (1H), 6.45 (1H) ppm.

EXAMPLE 13a

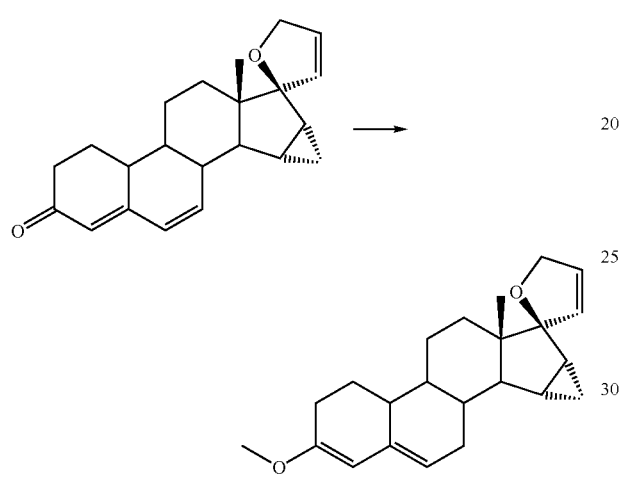

Analogously to Example 11a, 1.66 g of the compound prepared according to Example 12 are reacted, and after workup and purification 1.13 g of the title compound are isolated.

EXAMPLE 14

7α-Methyl-15α,16α-methylene-17α-(1'-propenyl)-17β-3'-oxidoestra-4-en-3-one (A) and 7β-methyl-15α,16α-methylene-17α-(1'-propenyl)-17β-3'-oxidoestra-4-en-3-one (B)

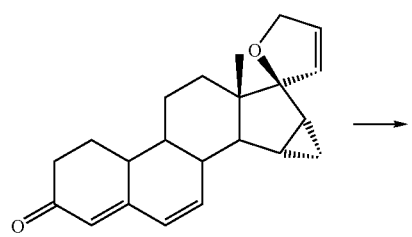

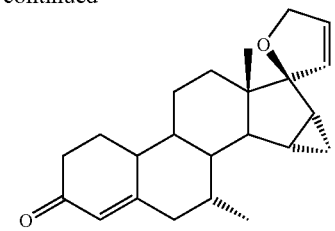

Analogously to Example 4, 250 mg of the compound prepared according to Example 13 are reacted, and after workup and purification 130 mg of the title compound A are isolated, as well as a still unpurified mixture which contains quantities of the title compound B.

$^{1}$H-NMR (CD$_2$Cl$_2$) of A: δ=0.59 (1H), 0.74 (1H), 0.87 (3H), 0.92-1.33 (6H), 1.22 (3H), 0.48-1.62 (2H), 1.76-1.88 (2H), 2.08 (1H), 2.23-2.41 (5H), 2.58 (1H), 4.56 (1H), 4.64 (1H), 5.76-5.83 (2H), 5.95 (1H) ppm.

EXAMPLE 15

7α-Ethyl-15α,16α-methylene-17α-(1'-propenyl)-17β-3'-oxidoestra-4-en-3-one (A) and 7β-ethyl-15α,16α-methylene-17α-(1'-propenyl)-17β-3'-oxidoestra-4-en-3-one (B)

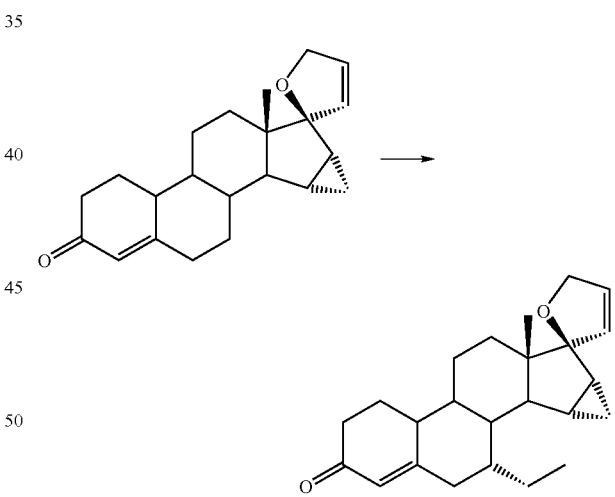

Analogously to Example 4, 250 mg of the compound prepared according to Example 13 are reacted using ethylmagnesium chloride, and after workup and purification 58 mg of the title compound A and 5.7 mg of the title compound B are isolated.

$^{1}$H-NMR (CDCl$_3$) of A: δ=0.53 (1H), 0.78 (1H), 0.86-1.27 (7H), 0.90 (3H), 1.17 (3H), 1.34-1.56 (3H), 1.72-1.86 (2H), 1.93 (1H), 2.05 (1H), 2.17-2.37 (4H), 2.58 (1H), 4.52 (1H), 4.59 (1H), 5.74 (1H), 5.78 (1H), 5.90 (1H) ppm.

$^{1}$H-NMR (CDCl$_3$) of B: δ=0.59 (1H), 0.64 (1H), 0.75 (1H), 0.91 (3H), 0.94 (1H), 1.04 (1H), 1.17 (3H), 1.19-1.74 (9H), 1.96 (1H), 2.07-2.35 (5H), 2.46 (1H), 4.52 (1H), 4.59 (1H), 5.71 (1H), 5.75 (1H), 5.90 (1H) ppm.

EXAMPLE 16

7α-vinyl-15α,16α-methylene-17α-(1'-propenyl)-17β-3'-oxidoestra-4-en-3-one (A) and 7β-vinyl-15α,16α-methylene-17α-(1'-propenyl)-17β-3'-oxidoestra-4-en-3-one (B)

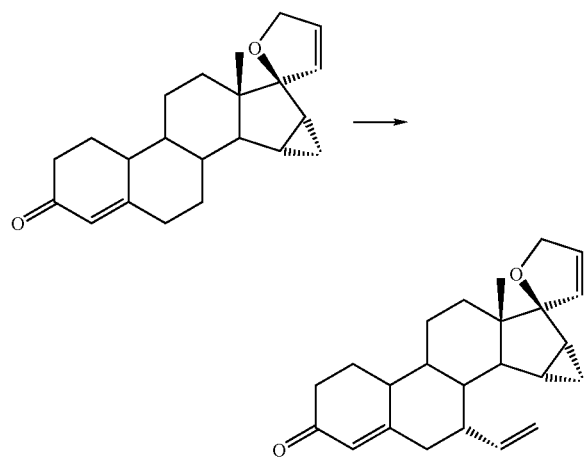

Analogously to Example 4, 250 mg of the compound prepared according to Example 13 are reacted using vinylmagnesium chloride, and after workup and purification 21.4 mg of the title compound A and 4.1 mg of the title compound B are isolated.

$^1$H-NMR (CD$_2$Cl$_2$) of A: δ=0.46 (1H), 0.65 (1H), 0.88-1.06 (3H), 1.17 (3H), 1.13-1.30 (2H), 1.44-1.87 (4H), 2.11 (1H), 2.19-2.37 (3H), 2.48 (1H), 2.60 (1H), 2.79 (1H), 4.51 (1H), 4.58 (1H), 5.09 (1H), 5.18 (1H), 5.32 (1H), 5.67-5.77 (2H), 5.79 (1H), 5.88 (1H) ppm.

$^1$H-NMR (CD$_2$Cl$_2$) of B: δ=0.47 (1H), 0.66 (1H), 0.73-0.81 (2H), 1.06 (1H), 1.15 (3H), 1.17-1.65 (7H), 1.73 (1H), 2.00-2.37 (6H), 4.51 (1H), 4.58 (1H), 4.92 (1H), 5.06 (1H), 5.70 (1H), 5.76 (1H), 5.86-5.99 (2H) ppm.

EXAMPLE 17

7α-Cyclopropyl-15α,16α-methylene-17α-(1'-propenyl)-17β-3'-oxidoestra-4-en-3-one (A) and 7β-cyclopropyl-15α,16α-methylene-17α-(1'-propenyl)-17β-3'-oxidoestra-4-en-3-one (B)

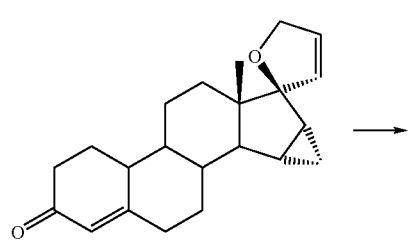

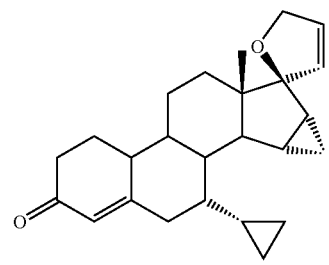

Analogously to Example 4, 250 mg of the compound prepared according to Example 13 are reacted using cyclopropylmagnesium bromide, and after workup and purification 47 mg of the title compound A and 5.3 mg of the title compound B are isolated.

$^1$H-NMR (CD$_2$Cl$_2$) of A: δ=-0.07 (1H), 0.35-0.62 (5H), 0.93-1.30 (8H), 1.17 (3H), 1.48-1.62 (2H), 1.77-1.89 (2H), 2.11 (1H), 2.22-2.38 (3H), 2.44 (1H), 2.53 (1H), 4.51 (1H), 4.60 (1H), 5.77 (1H), 5.82 (1H), 5.91 (1H) ppm.

$^1$H-NMR (CD$_2$Cl$_2$) of B: δ=0.02 (1H), 0.40-0.73 (7H), 0.94-1.04 (2H), 1.19 (3H), 1.22-1.30 (4K), 1.52-1.77 (4H), 2.08-2.30 (5H), 2.58 (1H), 4.52 (1H), 4.60 (1H), 5.71-5.74 (2H), 5.90 (1H) ppm.

EXAMPLE 18

Inert depot systems amenable to intrauterine implantation and composed of a biodegradable polymer or a synthetic silicone polymer consisting of an active ingredient-containing core in the appropriate polymer-active ingredient mixing ratio, surrounded by a polymer membrane ensuring the desired daily release rate, are introduced into the lumen of the rat uterus. The female animals are castrated beforehand and pretreated with estradiol for three days. The implants of different length (5-20 mm) and a restricted diameter (1.1 to 2 mm) remain for between 4 and 14 days in the rat uterus in order to investigate the local and systemic progestational effect of the released active ingredient on the basis of various parameters in different tissues. The following parameters are measured: 1) local progestational effect on the uterus on the basis of the weight of the uterus, the histologically detectable epithelial height and the expression of progestogen-regulated marker genes (e.g. IGFBP-1); 2) systemic progestational effect on the mammary gland on the basis of the expression of progestogen-regulated marker genes (e.g. RankL), 3) systemic progestational effect on the pituitary on the basis of the LH level (reduction in the estrogen-induced elevation of the LH level).

The compounds of the present invention show a significant progestational effect in the uterus which is comparable to a corresponding treatment with a levonorgestrel-containing depot system such as MIRENA®.

TABLE 1

Receptor binding values

| Ex. | Structure | Progesterone receptor (PR) | | Mineralocorticoid receptor (MR) | | Androgen receptor | | CF PR/ CF MR |
|---|---|---|---|---|---|---|---|---|
| | | IC50 [nM] | Competition factor | Competition factor | IC50 [nM] | Competition factor | | |
| | | 41.4 | 2.7 | 0.5 | 630 | 3.7 | | 5.40 |
| 1 | | 27 | 1.04 | 1.8 | 160 | 17.8 | | 0.58 |
| 2 | | 470 | 8.69 | 3.6 | 150 | 16.3 | | 2.41 |

TABLE 1-continued
| | | | | | | | | |
|---|---|---|---|---|---|---|---|---|
| 3 | 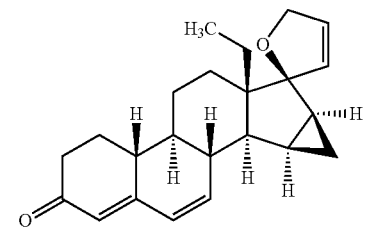 | Chiral | 53 | 2.43 | 3.4 | 410 | 19.3 | 0.71 |
| 4A | 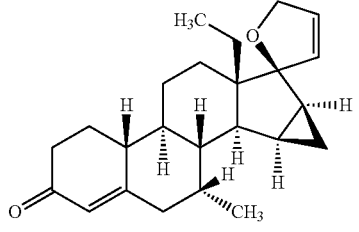 | Chiral | | 1.89 | 3.8 | 78 | 3.2 | 0.50 |
| 5A | 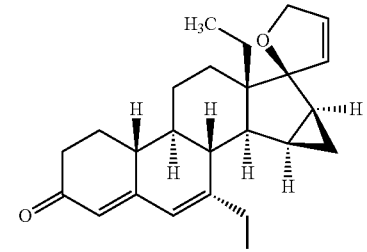 | Chiral | 140 | 6.15 | 2.3 | 100 | 5.4 | 2.67 |
| 5B | 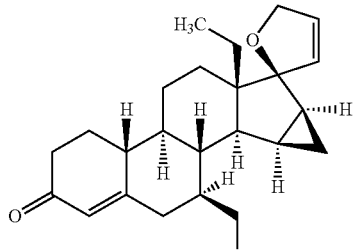 | Chiral | 130 | 6.03 | 15.0 | 990 | 42.8 | 0.40 |

TABLE 1-continued
| | | | | | | | |
|---|---|---|---|---|---|---|---|
| 6A | | | 44 | 4.30 | 1.8 | 56 | 3.1 | 2.39 |
| 7A | 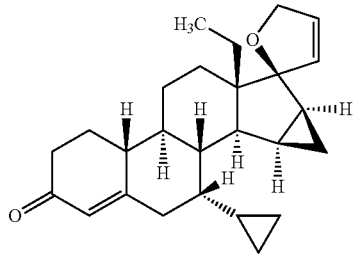 Chiral | 120 | 4.42 | 4.4 | 240 | 8.4 | 1.00 |
| 8 | 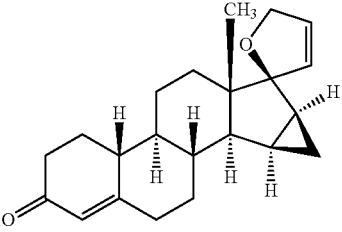 Chiral | 24 | 1.03 | 1.8 | 72 | 4.0 | 0.57 |
| 9 | 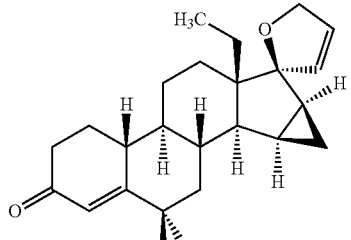 Chiral | 480 | 19.95 | 1.1 | 8600 | 480.7 | 18.14 |

TABLE 1-continued
| | | | | | | | | |
|---|---|---|---|---|---|---|---|---|
| 10 | 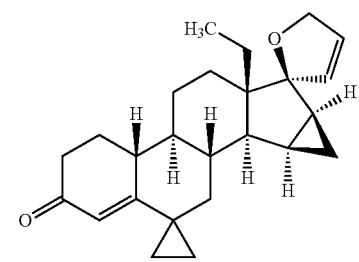 | Chiral | 33 | 1.08 | 0.8 | 53 | 2.8 | 1.35 |
| 11 | 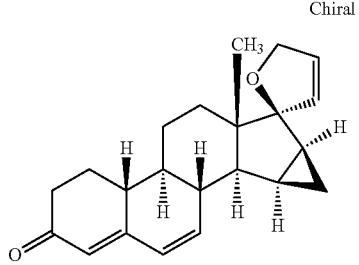 | Chiral | | | | | | |
| 12 | 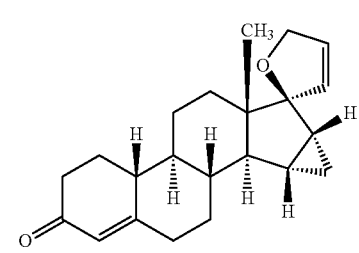 | Chiral | 29 | 0.79 | 1.0 | 6 | 120.0 | 0.79 |
| 13 | 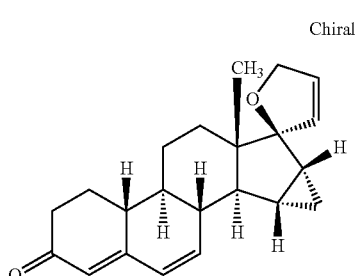 | Chiral | 56 | 2.04 | 0.9 | 2100 | 74.7 | 2.27 |

TABLE 1-continued
| | | | | | | | | |
|---|---|---|---|---|---|---|---|---|
| 14A | | 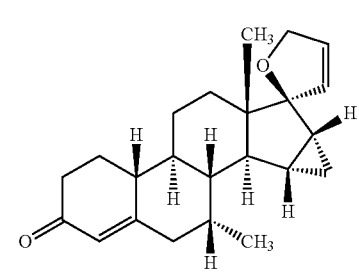 Chiral | 44 | 1.60 | 3.1 | 82 | 2.9 | 0.52 |
| 15A | | 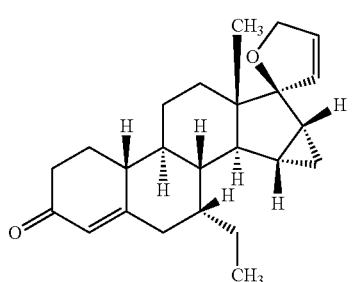 Chiral | 56 | 2.31 | 3.7 | 85 | 3.8 | 0.62 |
| 15B | | 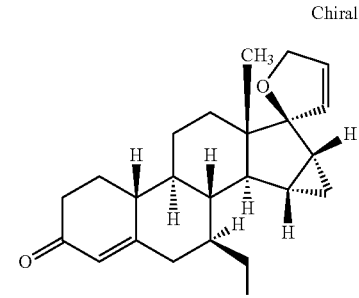 Chiral | | | | | | |
| 16A | | 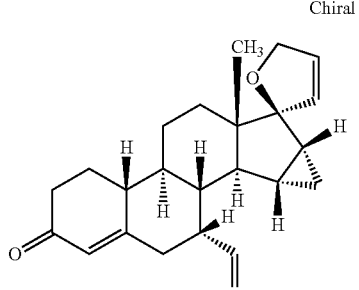 Chiral | 40 | 1.66 | 10.5 | 77 | 3.7 | 0.16 |

TABLE 1-continued

| | | | | | | | |
|---|---|---|---|---|---|---|---|
| 16B | Chiral | | | | | | |
| 17A | Chiral | 13 | 0.59 | 2.5 | 15 | 1.0 | 0.24 |
| 17B | | | | | | | |

TABLE 2
In vitro transactivation values
| Ex. | Structure | | In vitro transactivation | | | | | | |
|---|---|---|---|---|---|---|---|---|---|
| | | | Progesterone receptor (PR) | | Mineralo-corticoid receptor (MR) | | Androgen receptor | | | |
| | | | Agonism EC50 [nM] | Agonist activity [%] | Antagonism IC50 [nM] | Antagonist activity [%] | Agonism EC50 [nM] | Agonist activity [%] | Antagonism IC50 [nM] | Antagonist activity [%] |
| A | 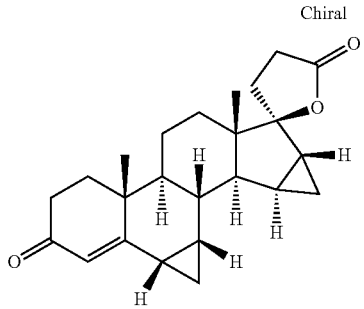 Chiral | 88 | 72.2 | 3.3 | 64.1 | 112.5 | 24.26 | 27 | 54.58 |
| 1 | 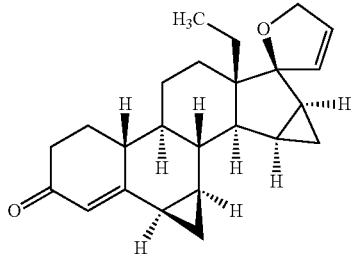 Chiral | | | Partial Agonist | | 9 | 68 | 11 | 35.3 |
| 2 | 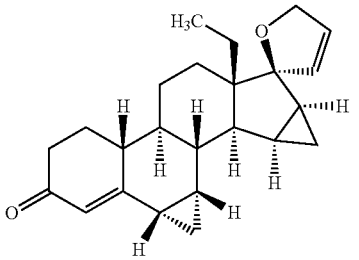 Chiral | | | 35 | 118.8 | 4.8 | 51.5 | 41 | 47.8 |

TABLE 2-continued

| | Structure | | | | | | | | |
|---|---|---|---|---|---|---|---|---|---|
| 3 | (Chiral steroid structure) | Chiral | | | 110 | 71.0 | 39 | 60.32 | 1000 | 5 |
| 4A | (Chiral steroid structure) | Chiral | 0.8 | 23.2 | 9 | 44.5 | 3.2 | 80.97 | 1000 | 5 |
| 5A | (Chiral steroid structure) | Chiral | 13.0 | 20.6 | 140 | 100.2 | 4.6 | 81.2 | 1000 | 5 |
| 5B | (Chiral steroid structure) | Chiral | 36.0 | 23.2 | 130 | 67.7 | 100 | 23.9 | 130 | 63.82 |
| 6A | | | 7.8 | 34.6 | 5 | 123.1 | 1.9 | 93.47 | 1000 | 5 |

TABLE 2-continued
| | | | | | | | | | |
|---|---|---|---|---|---|---|---|---|---|
| 7A | 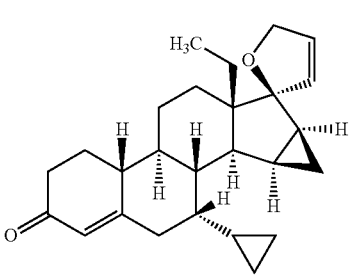 | Chiral | 7.5 | 37.1 | Partial Agonist | 17 | 82.3 | 1000 | 5 |
| 8 | 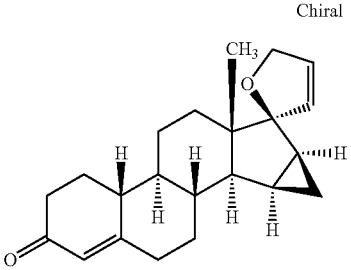 | Chiral | 1.6 | 77.5 | 95 | 106.2 | 10 | 58.71 | 1000 | 5 |
| 9 | 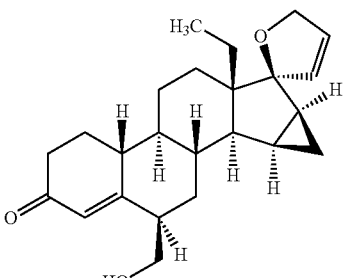 | Chiral | 1000.0 | 21.0 | 90 | 89.8 | 1000 | 19.66 | 140 | 48.11 |
| 10 | 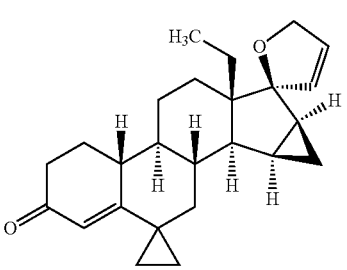 | Chiral | 0.1 | 45.2 | Partial Agonist | 1.2 | 106.55 | 1000 | 5 |

| | | | | | | | | |
|---|---|---|---|---|---|---|---|---|
| 11 | [structure] | Chiral | | | | | | | |
| 12 | [structure] | Chiral | 0.1 | 71.1 | Agonistic | 41 | 62.66 | 1000 | 5 |
| 13 | [structure] | Chiral | 8.4 | 62.8 | 46 | 86.1 | 200 | 10.57 | 130 | 81.32 |
| 14A | [structure] | Chiral | 0.7 | 96.0 | 72 | 60.9 | 4.6 | 56.06 | 1000 | 5 |

TABLE 2-continued

| | | | | | | | | |
|---|---|---|---|---|---|---|---|---|
| 15A | [steroid structure, Chiral] | 0.9 | 52.9 | Agonistic | 9.3 | 73.74 | 1000 | 5 |
| 15B | [steroid structure, Chiral] | | | | | | | |
| 16A | [steroid structure, Chiral] | 1.0 | 74.1 | Partial Agonistic | 4.4 | 72.56 | 1000 | 5 |
| 16B | [steroid structure, Chiral] | | | | | | | |

TABLE 2-continued

| | | | | | | | | | | |
|---|---|---|---|---|---|---|---|---|---|---|
| 17A | 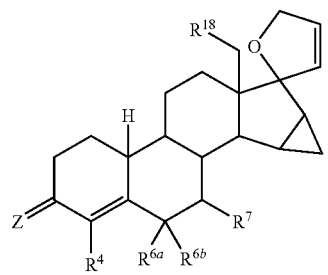 | Chiral | 4.5 | 82.7 | 110 | 71.5 | 11 | 65.81 | 1000 | 5 |
| 17B | | | | | | | | | | |

The invention claimed is:

1. A 15,16-Methylene-17-(1'-propenyl)-17-3'-oxidoestra-4-en-3-one derivative with the general chemical formula I

I in which
Z is oxygen, two hydrogen atoms, NOR', or NNHSO$_2$R', where R' is hydrogen, $C_1$-$C_{10}$ alkyl, aryl or $C_7$-$C_{20}$ aralkyl, and
$R^4$ is hydrogen or halogen,
and further, either:
$R^{6a}$, $R^{6b}$ are each mutually independently hydrogen, $C_1$-$C_{10}$ alkyl, $C_2$-$C_{10}$ alkenyl, or $C_2$-$C_{10}$ alkynyl, or together form methylene or 1,2-ethanediyl and $R^7$ is hydrogen, $C_1$-$C_{10}$ alkyl, $C_3$-$C_6$-cycloalkyl, $C_2$-$C_{10}$ alkenyl or $C_2$-$C_{10}$ alkynyl,
or:
$R^{6a}$, $R^7$ together comprise oxygen or a methylene group or are omitted, with the formation of a double bond between $C^6$ and $C^7$ and
$R^{6b}$ is hydrogen, $C_1$-$C_{10}$ alkyl, $C_2$-$C_{10}$ alkenyl or $C_2$-$C_{10}$ alkynyl and
$R^{18}$ is hydrogen or $C_1$-$C_3$ alkyl,
and solvates, hydrates and salts thereof and including all crystal modifications and all stereoisomers.

2. The 15,16-Methylene-17-(1'-propenyl)-17-3'-oxidoestra-4-en-3-one derivative as claimed in claim 1, characterized in that Z is oxygen, NOR' or NNHSO$_2$R'.

3. The 15,16-Methylene-17-(1'-propenyl)-17-3'-oxidoestra-4-en-3-one derivative as claimed in claim 1, characterized in that Z is oxygen.

4. The 15,16-Methylene-17-(1'-propenyl)-17-3'-oxidoestra-4-en-3-one derivative as claimed in claim 1, characterized in that $R^4$ is hydrogen or chlorine.

5. The 15,16-Methylene-17-(1'-propenyl)-17-3'-oxidoestra-4-en-3-one derivative as claimed in claim 1, characterized in that $R^{6a}$ and $R^{6b}$ together form 1,2-ethanediyl or are each hydrogen.

6. The 15,16-Methylene-17-(1'-propenyl)-17-3'-oxidoestra-4-en-3-one derivative as claimed in claim 1, characterized in that $R^7$ is hydrogen, methyl, ethyl, or vinyl.

7. The 15,16-Methylene-17-(1'-propenyl)-17-3'-oxidoestra-4-en-3-one derivative as claimed in claim 1, characterized in that $R^{6a}$ and $R^7$ together form a methylene group.

8. The 15,16-Methylene-17-(1'-propenyl)-17-3'-oxidoestra-4-en-3-one derivative as claimed in claim 1, characterized in that $R^{6a}$ and $R^7$ are omitted, with the formation of a double bond between $C^6$ and $C^7$.

9. The 15,16-Methylene-17-(1'-propenyl)-17-3'-oxidoestra-4-en-3-one derivative as claimed in claim 1, characterized in that $R^{18}$ is hydrogen or methyl.

10. The 15,16-Methylene-17-(1'-propenyl)-17-3'-oxidoestra-4-en-3-one derivative as claimed in claim 1, that is
17α-(1'-propenyl)-15α,16α-methylene-17β-3'-oxidoestra-4-en-3-one;
17α-(1'-propenyl)-15β,16β-methylene-17β-3'-oxidoestra-4-en-3-one;
7α-methyl-15α,16α-methylene-17α-(1'-propenyl)-17β-3'-oxidoestra-4-en-3-one;
7β-methyl-15α,16α-methylene-17α-(1'-propenyl)-17β-3'-oxidoestra-4-en-3-one;
7α-methyl-15β,16β-methylene-17α-(1'-propenyl)-17β-3'-oxidoestra-4-en-3-one;
7β-methyl-15β,16β-methylene-17α-(1'-propenyl)-17β-3'-oxidoestra-4-en-3-one;
7α-ethyl-15α,16α-methylene-17α-(1'-propenyl)-17β-3'-oxidoestra-4-en-3-one;
7β-ethyl-15α,16α-methylene-17α-(1'-propenyl)-17β-3'-oxidoestra-4-en-3-one;
7α-ethyl-15β,16β-methylene-17α-(1'-propenyl)-17β-3'-oxidoestra-4-en-3-one;
7β-ethyl-15β,16β-methylene-17α-(1'-propenyl)-17β-3'-oxidoestra-4-en-3-one;
7α-vinyl-15α,16α-methylene-17α-(1'-propenyl)-17β-3'-oxidoestra-4-en-3-one;
7β-vinyl-15α,16α-methylene-17α-(1'-propenyl)-17β-3'-oxidoestra-4-en-3-one;
7α-vinyl-15β,16β-methylene-17α-(1'-propenyl)-17β-3'-oxidoestra-4-en-3-one;

7β-vinyl-15β,16β-methylene-17α-(1'-propenyl)-17β-3'-oxidoestra-4-en-3-one;
7α-cyclopropyl-15α,16α-methylene-17α-(1'-propenyl)-17β-3'-oxidoestra-4-en-3-one;
7β-cyclopropyl-15α,16α-methylene-17α-(1'-propenyl)-17β-3'-oxidoestra-4-en-3-one;
7α-cyclopropyl-15β,16β-ethylene-17α-(1'-propenyl)-17β-3'-oxidoestra-4-en-3-one;
7β-cyclopropyl-15β,16β-methylene-17α-(1'-propenyl)-17β-3'-oxidoestra-4-en-3-one;
6-methylene-15α,16α-methylene-17α-(1'-propenyl)-17β-3'-oxidoestra-4-en-3-one;
6-methylene-15β,16β-ethylene-17α-(1'-propenyl)-17β-3'-oxidoestra-4-en-3-one;
6α-hydroxymethylene-15α,16α-methylene-17α-(1'-propenyl)-17β-3'-oxidoestra-4-en-3-one;
6β-hydroxymethylene-15α,16α-methylene-17α-(1'-propenyl)-17β-3'-oxidoestra-4-en-3-one;
6α-hydroxymethylene-15β,16β-ethylene-17α-(1'-propenyl)-17β-3'-oxidoestra-4-en-3-one;
6β-hydroxymethylene-15β,16β-ethylene-17α-(1'-propenyl)-17β-3'-oxidoestra-4-en-3-one;
6,6-(1,2-ethanediyl)-15α,16α-methylene-17α-(1'-propenyl)-17β-3'-oxidoestra-4-en-3-one;
6,6-(1,2-ethanediyl)-15β,16β-ethylene-17α-(1'-propenyl)-17β-3'-oxidoestra-4-en-3-one;
6α,7α;15α,16α-bismethylene-17α-(1'-propenyl)-17β-3'-oxidoestra-4-en-3-one;
6β,7β;15α,16α-bismethylene-17α-(1'-propenyl)-17β-3'-oxidoestra-4-en-3-one;
6α,7α;15β,16β-bismethylene-17α-(1'-propenyl)-17β-3'-oxidoestra-4-en-3-one;
6β,7β;15β,16β-bismethylene-17α-(1'-propenyl)-17β-3'-oxidoestra-4-en-3-one;
17α-(1'-propenyl)-15α,16α-methylene-17β-3'-oxidoestra-4,6-dien-3-one;
17α-(1'-propenyl)-15β,16β-ethylene-17β-3'-oxidoestra-4,6-dien-3-one;
(E/Z)-3-(hydroxyimino)-17α-(1'-propenyl)-15α,16α-methylene-17β-3'-oxido-estra-4-ene;
(E/Z)-3-(hydroxyimino)-17α-(1'-propenyl)-15β,16β-methylene-17β-3'-oxido-estra-4-ene;
(E/Z)-3-(hydroxyimino)-7α-methyl-15α,16α-methylene-17α-(1'-propenyl)-17β-3'-oxidoestra-4-ene;
(E/Z)-3-(hydroxyimino)-7β-methyl-15α,16α-methylene-17α-(1'-propenyl)-17β-3'-oxidoestra-4-ene;
(E/Z)-3-(hydroxyimino)-7α-methyl-15β,16β-methylene-17α-(1'-propenyl)-17β-3'-oxidoestra-4-ene;
(E/Z)-3-(hydroxyimino)-7β-methyl-15β,16β-methylene-17α-(1'-propenyl)-17β-3'-oxidoestra-4-ene;
(E/Z)-3-(hydroxyimino)-7α-ethyl-15α,16α-methylene-17α-(1'-propenyl)-17β-3'-oxidoestra-4-ene;
(E/Z)-3-(hydroxyimino)-7β-ethyl-15α,16α-methylene-17α-(1'-propenyl)-17β-3'-oxidoestra-4-ene;
(E/Z)-3-(hydroxyimino)-7α-ethyl-15β,16β-methylene-17α-(1'-propenyl)-17β-3'-oxidoestra-4-ene;
(E/Z)-3-(hydroxyimino)-7β-ethyl-15β,16β-methylene-17α-(1'-propenyl)-17β-3'-oxidoestra-4-ene;
(E/Z)-3-(hydroxyimino)-7α-vinyl-15α,16α-methylene-17α-(1'-propenyl)-17β-3'-oxidoestra-4-ene;
(E/Z)-3-(hydroxyimino)-7β-vinyl-15α,16α-methylene-17α-(1'-propenyl)-17β-3'-oxidoestra-4-ene;
(E/Z)-3-(hydroxyimino)-7α-vinyl-15β,16β-methylene-17α-(1'-propenyl)-17β-3'-oxidoestra-4-ene;
(E/Z)-3-(hydroxyimino)-7β-vinyl-15β,16β-methylene-17α-(1'-propenyl)-17β-3'-oxidoestra-4-ene;
(E/Z)-3-(hydroxyimino)-7α-cyclopropyl-15α,16α-methylene-17α-(1'-propenyl)-17β-3'-oxidoestra-4-ene;
(E/Z)-3-(hydroxyimino)-7β-cyclopropyl-15α,16α-methylene-17α-(1'-propenyl)-17β-3'-oxidoestra-4-ene;
(E/Z)-3-(hydroxyimino)-7α-cyclopropyl-15β,16β-ethylene-17α-(1'-propenyl)-17β-3'-oxidoestra-4-ene;
(E/Z)-3-(hydroxyimino)-7β-cyclopropyl-15β,16β-ethylene-17α-(1'-propenyl)-17β-3'-oxidoestra-4-ene;
(E/Z)-3-(hydroxyimino)-6-methylene-17α-(1'-propenyl)-15α,16α-methylene-17β-3'-oxidoestra-4-ene;
(E/Z)-3-(hydroxyimino)-6-methylene-17α-(1'-propenyl)-15β,16β-ethylene-17β-3'-oxidoestra-4-ene;
(E/Z)-3-(hydroxyimino)-6α-hydroxymethylene-17α-(1'-propenyl)-15α,16α-methylene-17β-3'-oxidoestra-4-ene;
(E/Z)-3-(hydroxyimino)-6β-hydroxymethylene-17α-(1'-propenyl)-15α,16α-methylene-17β-3'-oxidoestra-4-ene;
(E/Z)-3-(hydroxyimino)-6α-hydroxymethylene-17α-(1'-propenyl)-15β,16β-ethylene-17β-3'-oxidoestra-4-ene;
(E/Z)-3-(hydroxyimino)-6β-hydroxymethylene-17α-(1'-propenyl)-15β,16β-ethylene-17β-3'-oxidoestra-4-ene;
(E/Z)-3-(hydroxyimino)-6,6-(1,2-ethanediyl)-17α-(1'-propenyl)-15α,16α-methylene-17β-3'-oxidoestra-4-ene;
(E/Z)-3-(hydroxyimino)-6,6-(1,2-ethanediyl)-17α-(1'-propenyl)-15β,16β-methylene-17β-3'-oxidoestra-4-ene;
(E/Z)-3-(hydroxyimino)-6α,7α;15α,16α-bismethylene-17α-(1'-propenyl)-17β-3'-oxidoestra-4-ene;
(E/Z)-3-(hydroxyimino)-6β,7β;15α,16α-bismethylene-17α-(1'-propenyl)-17β-3'-oxidoestra-4-ene;
(E/Z)-3-(hydroxyimino)-6α,7α;15β,16β-bismethylene-17α-(1'-propenyl)-17β-3'-oxidoestra-4-ene;
(E/Z)-3-(hydroxyimino)-6β,7β;15β,16β-bismethylene-17α-(1'-propenyl)-17β-3'-oxidoestra-4-ene;
(E/Z)-3-(hydroxyimino)-17α-(1'-propenyl)-15β,16β-methylene-17β-3'-oxidoestra-4,6-diene;
(E/Z)-3-(hydroxyimino)-17α-(1'-propenyl)-15β,16β-methylene-17β-3'-oxidoestra-4,6-diene;
17α-(1'-propenyl)-18-methyl-15α,16α-methylene-17β-3'-oxidoestra-4-en-3-one;
17α-(1'-propenyl)-18-methyl-15β,16β-methylene-17β-3'-oxidoestra-4-en-3-one;
7α,18-dimethyl-15α,16α-methylene-17α-(1'-propenyl)-17β-3'-oxidoestra-4-en-3-one;
7β,18-dimethyl-15α,16α-methylene-17α-(1'-propenyl)-17β-3'-oxidoestra-4-en-3-one;
7α,18-dimethyl-15β,16β-methylene-17α-(1'-propenyl)-17β-3'-oxidoestra-4-en-3-one;
7β,18-dimethyl-15β,16β-methylene-17α-(1'-propenyl)-17β-3'-oxidoestra-4-en-3-one;
7α-ethyl-18-methyl-15α,16α-methylene-17α-(1'-propenyl)-17β-3'-oxidoestra-4-en-3-one;
7β-ethyl-18-methyl-15α,16α-methylene-17α-(1'-propenyl)-17β-3'-oxidoestra-4-en-3-one;
7α-ethyl-18-methyl-15β,16β-methylene-17α-(1'-propenyl)-17β-3'-oxidoestra-4-en-3-one;
7β-ethyl-18-methyl-15β,16β-methylene-17α-(1'-propenyl)-17β-3'-oxidoestra-4-en-3-one;
7α-vinyl-18-methyl-15α,16α-methylene-17α-(1'-propenyl)-17β-3'-oxidoestra-4-en-3-one;
7β-vinyl-18-methyl-15α,16α-methylene-17α-(1'-propenyl)-17β-3'-oxidoestra-4-en-3-one;
7α-vinyl-18-methyl-15β,16β-methylene-17α-(1'-propenyl)-17β-3'-oxidoestra-4-en-3-one;

7β-vinyl-18-methyl-15β,16β-methylene-17α-(1-propenyl)-17β-3'-oxidoestra-4-en-3-one;
7α-cyclopropyl-18-methyl-15α,16α-methylene-17α-(1'-propenyl)-17β-3'-oxidoestra-4-en-3-one;
7β-cyclopropyl-18-methyl-15α,16α-methylene-17α-(1-propenyl)-17β-3'-oxidoestra-4-en-3-one;
7α-cyclopropyl-18-methyl-15β,16β-methylene-17α-(1'-propenyl)-17β-3'-oxidoestra-4-en-3-one;
7β-cyclopropyl-18-methyl-15β,16β-methylene-17α-(1'-propenyl)-17β-3'-oxidoestra-4-en-3-one;
6-methylene-18-methyl-15α,16α-methylene-17α-(1'-propenyl)-17β-3-oxido-estra-4-en-3-one;
6-methylene-18-methyl-15β,16β-methylene-17α-(1'-propenyl)-17β-3'-oxido-estra-4-en-3-one;
6α-hydroxymethylene-18-methyl-15α,16α-methylene-17α-(1'-propenyl)-17β-3-oxidoestra-4-en-3-one;
6β-hydroxymethylene-18-methyl-15α,16α-methylene-17α-(1-propenyl)-17β-3'-oxidoestra-4-en-3-one;
6α-hydroxymethylene-18-methyl-15β,16β-methylene-17α-(1'-propenyl)-17β-3'-oxidoestra-4-en-3-one;
6β-hydroxymethylene-18-methyl-15β,16β-methylene-17α-(1'-propenyl)-17β-3'-oxidoestra-4-en-3-one;
6,6-(1,2-ethanediyl)-18-methyl-15α,16α-methylene-17α-(1'-propenyl)-17β-3'-oxidoestra-4-en-3-one;
6,6-(1,2-ethanediyl)-18-methyl-15β,16β-methylene-17α-(1'-propenyl)-17β-3'-oxidoestra-4-en-3-one;
6α,7α; 15α,16α-bismethylene-18-methyl-17α-(1'-propenyl)-17β-3'-oxidoestra-4-en-3-one;
6β,7β;15α,16α-bismethylene-18-methyl-17α-(1'-propenyl)-17β-3'-oxidoestra-4-en-3-one;
6α,7α;15β,16β-bismethylene-18-methyl-17α-(1'-propenyl)-17β-3'-oxidoestra-4-en-3-one;
6β,7β;15β,16β-bismethylene-18-methyl-17α-(1'-propenyl)-17β-3'-oxidoestra-4-en-3-one;
17α-(1'-propenyl)-18-methyl-15α,16α-methylene-17β-3'-oxidoestra-4,6-dien-3-one;
17α-(1'-propenyl)-18-methyl-15β,16β-methylene-17β-3'-oxidoestra-4,6-dien-3-one;
(E/Z)-3-(hydroxyimino)-18-methyl-17α-(1'-propenyl)-15α,16α-methylene-17β-3'-oxidoestra-4-ene;
(E/Z)-3-(hydroxyimino)-18-methyl-17α-(1'-propenyl)-15β,16β-methylene-17β-3'-oxidoestra-4-ene;
(E/Z)-3-(hydroxyimino)-7α,18-bismethyl-15α,16α-methylene-17α-(1'-propenyl)-17β-3'-oxidoestra-4-ene;
(E/Z)-3-(hydroxyimino)-7β,18-bismethyl-15α,16α-methylene-17α-(1'-propenyl)-17β-3'-oxidoestra-4-ene;
(E/Z)-3-(hydroxyimino)-7α,18-bismethyl-15β,16β-methylene-17α-(1'-propenyl)-17β-3'-oxidoestra-4-ene;
(E/Z)-3-(hydroxyimino)-7β,18-bismethyl-15β,16β-methylene-17α-(1'-propenyl)-17β-3'-oxidoestra-4-ene;
(E/Z)-3-(hydroxyimino)-7α-ethyl-18-methyl-15α,16α-methylene-17α-(1'-propenyl)-17β-3'-oxidoestra-4-ene;
(E/Z)-3-(hydroxyimino)-7β-ethyl-18-methyl-15α,16α-methylene-17α-(1'-propenyl)-17β-3'-oxidoestra-4-ene;
(E/Z)-3-(hydroxyimino)-7α-ethyl-18-methyl-15β,16β-methylene-17α-(1'-propenyl)-17β-3'-oxidoestra-4-ene;
(E/Z)-3-(hydroxyimino)-7β-ethyl-18-methyl-15β,16β-methylene-17α-(1'-propenyl)-17β-3'-oxidoestra-4-ene;
(E/Z)-3-(hydroxyimino)-7α-vinyl-18-methyl-15α,16α-methylene-17α-(1'-propenyl)-17β-3'-oxidoestra-4-ene;
(E/Z)-3-(hydroxyimino)-7β-vinyl-18-methyl-15α,16α-methylene-17α-(1'-propenyl)-17β-3'-oxidoestra-4-ene;
(E/Z)-3-(hydroxyimino)-7α-vinyl-18-methyl-15β,16β-ethylene-17α-(1'-propenyl)-17β-3'-oxidoestra-4-ene;
(E/Z)-3-(hydroxyimino)-7β-vinyl-18-methyl-15β,16β-ethylene-17α-(1'-propenyl)-17β-3'-oxidoestra-4-ene;
(E/Z)-3-(hydroxyimino)-7α-cyclopropyl-18-methyl-15α,16α-methylene-17α-(1'-propenyl)-17β-3'-oxidoestra-4-ene;
(E/Z)-3-(hydroxyimino)-7β-cyclopropyl-18-methyl-15α,16α-methylene-17α-(1'-propenyl)-17β-3'-oxidoestra-4-ene;
(E/Z)-3-(hydroxyimino)-7α-cyclopropyl-18-methyl-15β,16β-ethylene-17α-(1'-propenyl)-17β-3'-oxidoestra-4-ene;
(E/Z)-3-(hydroxyimino)-7β-cyclopropyl-18-methyl-15β,16β-ethylene-17α-(1'-propenyl)-17β-3'-oxidoestra-4-ene;
(E/Z)-3-(hydroxyimino)-18-methyl-6-methylene-17α-(1'-propenyl)-15α,16α-methylene-17β-3'-oxidoestra-4-ene;
(E/Z)-3-(hydroxyimino)-18-methyl-6-methylene-17α-(1'-propenyl)-15β,16β-methylene-17β-3'-oxidoestra-4-ene;
(E/Z)-3-(hydroxyimino)-6α-hydroxymethylene-17α-(1'-propenyl)-18-methyl-15α,16α-methylene-17β-3'-oxidoestra-4-ene;
(E/Z)-3-(hydroxyimino)-6β-hydroxymethylene-17α-(1'-propenyl)-18-methyl-15α,16α-methylene-17β-3'-oxidoestra-4-ene;
(E/Z)-3-(hydroxyimino)-6α-hydroxymethylene-17α-(1'-propenyl)-18-methyl-15β,16β-methylene-17β-3'-oxidoestra-4-ene;
(E/Z)-3-(hydroxyimino)-6β-hydroxymethylene-17α-(1'-propenyl)-18-methyl-15β,16β-methylene-17β-3'-oxidoestra-4-ene;
(E/Z)-3-(hydroxyimino)-6,6-(1,2-ethanediyl)-17α-(1'-propenyl)-18-methyl-15α,16α-methylene-17β-3'-oxidoestra-4-ene;
(E/Z)-3-(hydroxyimino)-6,6-(1,2-ethanediyl)-17α-(1'-propenyl)-18-methyl-15β,16β-ethylene-17β-3'-oxidoestra-4-ene;
(E/Z)-3-(hydroxyimino)-6α,7α;15α,16α-bismethylene-18-methyl-17α-(1'-propenyl)-17β-3'-oxidoestra-4-ene;
(E/Z)-3-(hydroxyimino)-6β,7β;15α,16α-bismethylene-18-methyl-17α-(1'-propenyl)-17β-3'-oxidoestra-4-ene;
(E/Z)-3-(hydroxyimino)-6α,7α;15β,16β-bismethylene-18-methyl-17α-(1'-propenyl)-17β-3'-oxidoestra-4-ene;
(E/Z)-3-(hydroxyimino)-6β,7β;15β,16β-bismethylene-18-methyl-17α-(1'-propenyl)-17β-3'-oxidoestra-4-ene;
(E/Z)-3-(hydroxyimino)-17α-(1'-propenyl)-18-methyl-15α,16α-methylene-17-oxidoestra-4,6-diene; or
(E/Z)-3-(hydroxyimino)-17α-(1'-propenyl)-18-methyl-15β,16β-methylene-17β-3'-oxidoestra-4,6-diene.

11. A method for providing oral contraception or for the treatment of pre-, peri- and postmenopausal problems, said method comprising administering to the patient an effective amount of a 15,16-methylene-17-(1'-propenyl)-17-3'-oxidoestra-4-en-3-one compound according to claim 1.

12. The method as claimed in claim 11, characterized in that the drug has progestational, antimineralcorticoid and neutral to slight androgenic activity.

13. A pharmaceutical composition comprising at least one 15,16-methylene-17-(1'-propenyl)-17-3'-oxidoestra-4-en-3-one derivative as claimed in claim 1 and at least one pharmaceutically acceptable excipient.

14. The pharmaceutical composition as claimed in claim 13, further comprising at least one estrogen.

15. The pharmaceutical composition as claimed in claim 14, characterized in that the estrogen is ethynylestradiol.

16. The pharmaceutical composition as claimed in claim 14, characterized in that the estrogen is estradiol valerate.

17. The pharmaceutical composition as claimed in claim 14, characterized in that the estrogen is a natural estrogen.

18. The pharmaceutical composition as claimed in claim 17, characterized in that the natural estrogen is estradiol.

19. The pharmaceutical composition as claimed in claim 17, characterized in that the natural estrogen is a conjugated estrogen.

20. The method according to claim 12, wherein said 15,16-methylene-17-(1'-propenyl)-17-3'-oxidoestra-4-en-3-one compound is in a form suitable intrauterine administration.

21. The method as claimed in claim 20, wherein said compound is administered in the form of an intrauterine system (IUS).

22. An medicinal product comprising at least one 15,16-methylene-17-(1'-propenyl)-17-3'-oxidoestra-4-en-3-one derivative according to claim 1 and at least one pharmaceutically acceptable excipient.

23. The medicinal product as claimed in claim 22, that is an intrauterine system.

* * * * *